United States Patent
Pereira et al.

(10) Patent No.: US 7,202,204 B2
(45) Date of Patent: Apr. 10, 2007

(54) PERSONAL CARE PRODUCT CONTAINING DIESTER QUAT

(75) Inventors: Abel G. Pereira, Bridgewater, NJ (US); Duane St. Amour, South Amboy, NJ (US); Helena S. Barinova, North Brunswick, NJ (US)

(73) Assignee: Croda, Inc., Edison, NJ (US)

( * ) Notice: Subject to any disclaimer, the term of this patent is extended or adjusted under 35 U.S.C. 154(b) by 0 days.

(21) Appl. No.: 11/042,784

(22) Filed: Jan. 24, 2005

(65) Prior Publication Data

US 2005/0288198 A1    Dec. 29, 2005

Related U.S. Application Data

(63) Continuation of application No. 10/825,821, filed on Apr. 16, 2004, now abandoned.

(60) Provisional application No. 60/463,497, filed on Apr. 17, 2003.

(51) Int. Cl.
*C11D 1/62* (2006.01)
(52) U.S. Cl. ........................................ 510/504
(58) Field of Classification Search ............... None
See application file for complete search history.

(56) References Cited

U.S. PATENT DOCUMENTS

| | | | |
|---|---|---|---|
| 1,985,424 A | 12/1934 | Piggott | |
| 2,438,091 A | 3/1948 | Lynch | |
| 2,528,378 A | 10/1950 | Mannheimer | |
| 2,658,072 A | 11/1953 | Kosmin | |
| 2,965,576 A | 12/1960 | Wilson | |
| 3,155,591 A | 11/1964 | Hilfer | |
| 3,755,560 A | 8/1973 | Dickert et al. | |
| 3,929,678 A | 12/1975 | Laughlin et al. | |
| 3,959,461 A | 5/1976 | Bailey et al. | |
| 4,185,017 A | 1/1980 | Piesch et al. | |
| 4,275,055 A | 6/1981 | Nachtigal et al. | |
| 4,387,090 A | 6/1983 | Bolich, Jr. | |
| 4,421,769 A | 12/1983 | Dixon et al. | |
| 4,557,853 A | 12/1985 | Collins | |
| 4,704,272 A | 11/1987 | Oh et al. | |
| 4,741,855 A | 5/1988 | Grote et al. | |
| 4,788,006 A | 11/1988 | Bolich, Jr. et al. | |
| 4,902,499 A | 2/1990 | Bolish, Jr. et al. | |
| 4,919,934 A | 4/1990 | Deckner et al. | |
| 4,976,953 A | 12/1990 | Orr et al. | |
| 5,011,681 A | 4/1991 | Ciotti et al. | |
| 5,120,532 A | 6/1992 | Wells et al. | |
| 5,151,209 A | 9/1992 | McCall et al. | |
| 5,151,210 A | 9/1992 | Steuri et al. | |
| 5,302,377 A | 4/1994 | Pereira et al. | |
| 5,455,025 A | 10/1995 | Pereira et al. | |
| 5,463,094 A | 10/1995 | Brown | |
| 5,597,555 A | 1/1997 | Pereira et al. | |
| 5,681,915 A | 10/1997 | Lechner | |
| 5,693,316 A | 12/1997 | Pereira et al. | |
| 5,750,490 A | 5/1998 | Wilsch-Irrgang | |
| 5,854,201 A | 12/1998 | Behler | |
| 5,880,086 A | 3/1999 | Weinelt | |
| 5,961,966 A | 10/1999 | Abend | |
| 6,037,315 A | 3/2000 | Franklin | |
| 6,323,167 B1 | 11/2001 | Franklin | |
| 6,462,014 B1 | 10/2002 | Johnson et al. | |
| 6,465,419 B1 | 10/2002 | Bermejo Oses | |
| 6,476,254 B1 | 11/2002 | Pereira | |
| 6,502,325 B1 | 1/2003 | Zappone et al. | |
| 2003/0013627 A1 | 1/2003 | Bermejo Oses | |

FOREIGN PATENT DOCUMENTS

EP    0 095 238 A2    11/1983
WO    WO 03/063790    *    8/2003

* cited by examiner

*Primary Examiner*—John R. Hardee
(74) *Attorney, Agent, or Firm*—Lerner, David, Littenberg, Krumholz & Mentlik, LLP

(57) ABSTRACT

The present invention relates to a personal care product containing a mixture of at least one personal care ingredient and one diester quaternary ammonium compound with a pH between 4.0 and 10.0 and a viscosity between 100 and 300,000 cps, and the method of making the personal care product diester tertiary amines and quats are also described.

30 Claims, No Drawings

PERSONAL CARE PRODUCT CONTAINING DIESTER QUAT

CROSS-REFERENCE TO RELATED APPLICATIONS

The present application is a continuation of U.S. application Ser. No. 10/825,821, filed Apr. 16, 2004 now abandoned, and claims the benefit of U.S. Provisional Patent Application No. 60/463,497, filed Apr. 17, 2003, the disclosures of which are incorporated by reference herein.

BACKGROUND OF THE INVENTION

There are many known types of quaternary compounds or "quats" and they have been used in many fields. Quats can be tremendously useful compounds. Certain quats, however, are not particularly environmentally friendly. These quats break down very slowly and could constitute an environmental pollution. Because they have reactive nitrogen species, they can have previously unrecognized activity.

Other quats, such as ester quats, which contain ester linkages, are far more environmentally friendly in as much as they degrade much more readily. Ester quats are generally formed as mono, di, or tri esters, or a mixture of mono, di, or tri ester.

Ester quats are frequently used in laundry softeners because of their environmentally friendly properties. However, ester quats are often stable only in a relatively narrow and generally acidic range of pH. Ester quats used in laundry softeners have a generally acidic pH (pH of less than about 5.0). The ester quats used in laundry softeners are generally too acidic for use as a personal care product on the hair or skin. Ester quats are disclosed in, inter alia, U.S. Pat. Nos. 6,465,419, 6,462,014, 6,323,167, 6,037,315, 5,880,086, 5,854,201, 5,750,490, 5,681,915, and 5,463,094, and U.S. Published Patent Application No. U.S. 2003/0013627.

Certainly, compounds with improved environmental properties, improved stability in a higher pH and improved substantivity would therefore be highly desirable.

SUMMARY OF THE INVENTION

The present invention addresses these needs by providing personal care products that preferably have a pH of between about 4.0 and about 10.0, and more preferably about 5.0 and about 9.0, and a viscosity of between about 100 to about 300,000 centipois (cps). These personal care products, in accordance with one aspect of the present invention are a mixture including at least one personal care ingredient and a diester quat having the Formula I.

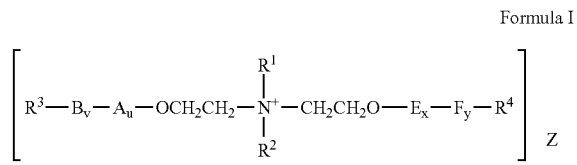

Formula I

In Formula I, $R^1$ and $R^2$ are the same or different, branched or straight chain, substituted or unsubstituted, saturated or unsaturated alkyl, cyclic or aromatic groups including between about 0 and about 22 carbon atoms. However, at least one of $R^1$ and $R^2$ must be at least $C_1$. In addition, if either $R^1$ and $R^2$ are $C_0$, then the molecule of Formula I is not a quat and is not positively charged. In such instances, no counter ion is needed. These tertiary amine esters are also contemplated as part of the invention.

A and E are the same or different and may be ethoxy, propoxy or butoxy groups. When propoxy or butoxy groups are used, they may be straight chain or branched. In a particularly preferred embodiment of the present invention, the compound of Formula I includes at least one propoxy or butoxy group, and most preferably at least one propoxy group. In Formula I, this is reflected in the fact that at least one A and/or at least one E group or unit is propoxy. The designations u and x may be the same or different and are each at least 2 and at most about 80 with the proviso that the number of ethoxy groups for each of A and E will be about 80 or less and the number of propoxy and butoxy groups for each of A and E is about 30 or less. That means that if all A units were ethoxy and all E units were propoxy that u could be 80 (a string of 80 ethoxy units) and x could be 30 (a string of 30 propoxy units). If A were a mixture of such alkoxy units, u could be 80 and of these, no more than about 30 A units of which could be propoxy. It is preferred that at least u or x be at least 2 and even more preferred that both u and x be at least 5. It is preferred that the majority of alkoxy units in Formula I be ethoxy units. For example, where u and x are each 2 and A and E are both 1 unit of propoxy and 1 unit of ethoxy, because of the ethoxy groups bound directly to the nitrogen, the majority of all alkoxy groups are ethoxy, 4 ethoxy groups to 2 propoxy groups. It is even more preferred that the number of ethoxy units in both A and E be in the majority.

B and F may be the same or different and are either of Formula II or Formula III.

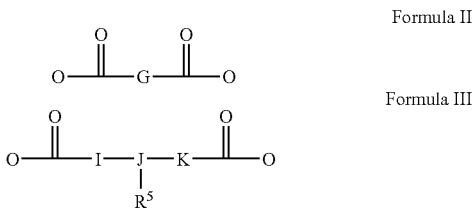

Formula II

Formula III

Formula II reflects a diacid or diprotic acid and Formula III reflects a tiacid or triportic acid. In Formula II and III, G is $C_0$ through $C_{36}$ groups which may be substituted or unsubstituted, saturated or unsaturated, straight or branched, alkyl, cyclic or aromatic. By "$C_0$" it should be clear that no carbon is necessary in that position. A "$C_{36}$" group is a molecule that includes 36 carbons and this general style of nomenclature will be used throughout. I and K are $C_0$ to $C_{18}$. J is preferably CH. $R^5$ is H or [—L—COO—$R^6$] where L can be saturated or unsaturated, substituted or unsubstituted, straight or branched, alkyl, cyclic or aromatic and can be a $C_0$–$C_{12}$ group; and v and y may be the same or different and are 0 or 1; when v equals 0, $R^3$ may be Formula IV

Formula IV a UV protecting group ending in a reactive carboxyl group or a poly fatty acid ending in a reactive carboxyl group. $R^7$ is branched or straight chain, substituted or unsubstituted, saturated or unsaturated alkyl (a chain of carbons such as an alkane or alkene), cyclic (a ring structure that does not have a resonance) or aromatic groups of $C_1$ to $C_{36}$ in total carbon atoms. Preferably, $R^7$ is a fatty substituent.

When y equals 0, $R^4$ may be selected from the same possible groups as discussed above for $R^3$.

When v equals 1, $R^3$ may be Formula V or VI

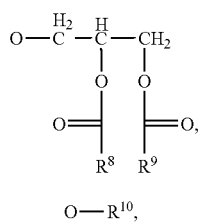

Formula V

Formula VI a UV protecting group ending in a reactive hydroxy group or a poly fatty acid ending in a reactive hydroxy group. $R^8$, $R^9$ and $R^{10}$ are the same or different, branched or straight chain, substituted or unsubstituted, saturated or unsaturated alkyl, cyclic or aromatic groups of $C_1$ to $C_{36}$ in total carbon atoms. Preferably, $R^8$, $R^9$ and $R^{10}$ are fatty substituents.

When y equals 1, $R^4$ may be Formula V or VI

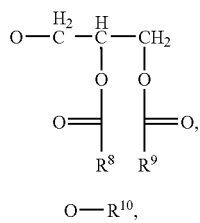

Formula V

Formula VI a UV protecting group ending in a reactive hydroxy group or a poly fatty acid ending in a reactive hydroxy group. $R^8$, $R^9$ and $R^{10}$ are the same or different, branched or straight chain, substituted or unsubstituted, saturated or unsaturated alkyl, cyclic or aromatic groups $C_1$ to $C_{36}$ in total carbon atoms. Preferably, $R^8$, $R^9$ and $R^{10}$ are fatty substituents.

When v or y is 1 and B or F are Formula III, $R^6$ is Formula V or VI

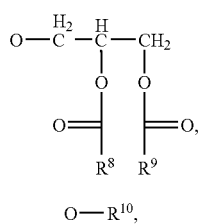

Formula V

Formula VI a UV protecting group ending in a reactive hydroxy group or a poly fatty acid ending in a reactive hydroxy group. $R^8$, $R^9$ and $R^{10}$ are the same or different, branched or straight chain, substituted or unsubstituted, saturated or unsaturated alkyl, cyclic or aromatic groups $C_1$ to $C_{36}$ in total carbon atoms. Preferably, $R^8$, $R^9$ and $R^{10}$ are fatty substituents.

In an alternative preferred embodiment, the majority of alkoxy units in Formula I are propoxy groups. For example, where u and x are each 2 and A and E are both completely propoxy, even with the ethoxy groups bound directly to the nitrogen, the majority of all alkoxy groups are propoxy, 4 propoxy groups to 2 ethoxy groups. It is even more preferred that both A and E be propoxy groups without any ethoxy groups as part of A or E.

The diester quats of Formula I are generally positively charged and are usually, but not always associated with a counter ion Z.

The at least one personal care ingredient can include, without limitation, any solvent, surfactant, conditioner, pigment, UV protector or UV protecting group, color, fragrance, dye, excipient or additive useful in formulating personal care products such as, without limitation, cosmetics, sun-screens and sun-blocks, shampoos, skin creams, gels or lotions, conditioners, softeners and the like.

Particularly preferred are those personal care products having a pH which ranges from between about 5.5 to about 8.5 and more preferably from about 6 to about 8. Also preferred are personal care products where the diester quat used has the Formula VII:

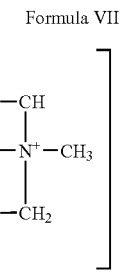

Formula VII

In Formula VII, the two $R^7$ groups are preferably a mixture of fatty substituents derived from using lanolin fatty acids. The present invention also relates to methods of making these products and to the diester tertiary amines and diester quats useful in these personal care products.

DETAILED DESCRIPTION

A diester quat in accordance with the present invention is a quaternary nitrogen containing compound which includes within two of its four bound substituent groups, ($R^1$, $R^2$, $R^3$—$B_v$—$A_u$—$O(CH_2)_2$— and $R^4$—$F_y$—$E_x$—$O(CH_2)_2$—) at least one ester group or ester linkage. More specifically, each of the groups $R^3$—$B_v$—$A_u$—$O(CH_2)_2$— and $R^4$—$F_y$—$E_x$—$O(CH_2)_2$— include at least one such ester group. It is possible, such as when, for example, v equals 1 and B is a triacid of Formula III that that substituent group would include three ester linkages.

Diester quats in accordance with the present invention include those having the Formula I.

Formula I

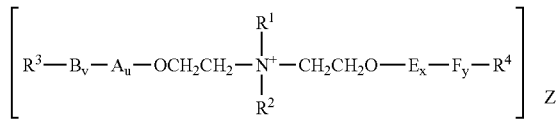

In Formula I, $R^1$ and $R^2$ are the same or different, branched or straight chain, substituted or unsubstituted, saturated or unsaturated alkyl, cyclic or aromatic groups including between about $C_1$ and about $C_{22}$ carbon atoms. $R^1$ and $R^2$ are preferably the same or different, branched or straight chain, substituted or unsubstituted, saturated or unsaturated alkyl, cyclic or aromatic groups including between about $C_1$ and $C_7$ carbon atoms. Most preferably, at lease one of $R^1$ and $R^2$ are methyl and most preferably both are methyl groups. It is possible that one, but not both, of $R^1$ and $R^2$ be $C_0$, in which case, using Formula I, there would be no positive change or counter ion. These tertiary diester amines are also contemplated.

A and E are the same or different and are alkoxy groups that are preferably ethoxy, propoxy or butoxy groups. Longer groups up to $C_8$ are also possible. When propoxy, butoxy or longer groups are used, they may be straight chain or branched. In a particularly preferred embodiment of the present invention, the compound of Formula I includes at least one propoxy or butoxy group, and most preferably at least one propoxy group. In Formula I, this is reflected in the fact that at least one A and/or at least one E group or unit is propoxy. The designations u and x may be the same or different and are at least 2 and at most about 80 with the proviso that the number of ethoxy groups for each of A and E will be about 80 or less and the number of propoxy and butoxy groups for A and E is about 30 or less. That means that if all A units were ethoxy and all E units were propoxy that u could be 80 (a string of 80 ethoxy units) and x could be 30 (a string of 30 propoxy units). If A were a mixture of such alkoxy units, u could be 80 no more than about 30 A units of which could be propoxy. It is preferred that at least u or x be at least 2 and more preferred that both u and x be at least 5. It is preferred that the majority of alkoxy units in Formula I be ethoxy units. For example, where u and x are each 2 and A and E are both 1 unit of propoxy and 1 unit of ethoxy, because of the ethoxy groups bound directly to the nitrogen (which are not part of A or E), the majority of all alkoxy groups in Formula I are ethoxy, 4 ethoxy groups to 2 propoxy groups. It is even more preferred that the number of ethoxy units in both A and E be in the majority. In another preferred embodiment, u and x may be the same or different and are at least 2 and at most about 30 and even more preferably u and x may be the same or different and are at least 2 and at most about 20 units. Most preferably, u and x are 5 and are composed of two blocks, the first block composed of 2 branched propoxy groups —($CH_2CH(CH_3)O$)— and the second block composed of 3 ethoxy groups —($CH_2CH_2O$)—.

In an alternative preferred embodiment, the majority of alkoxy units in Formula I are propoxy groups. For example, where u and x are each 2 and A and E are both completely propoxy, even with the ethoxy groups bound directly to the nitrogen, the majority of all alkoxy groups are propoxy, 4 propoxy groups to 2 ethoxy groups. It is even more preferred that both A and E be propoxy groups without any ethoxy groups as part of A or E.

B and F may be the same or different and are either of Formula II or Formula III.

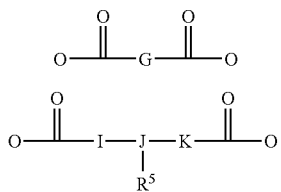

Formula II reflects a diacid or diprotic acid and Formula II reflects a tiacid or triportic acid. In Formula II and III, G is $C_0$ through $C_{36}$ groups which may be substituted or unsubstituted, saturated or unsaturated, straight or branched, alkyl, cyclic or aromatic. By "$C_0$" it should be clear that no carbon is necessary in that position. A "$C_{36}$" group is a molecule that includes 36 carbons and this general style of nomenclature will be used throughout. I and K can be $C_0$ to $C_{18}$ J is preferably CH. $R^5$ is H or [—L—COO—$R^6$] where L can be saturated or unsaturated, substituted or unsubstituted, straight or branched, alkyl, cyclic or aromatic and can be a $C_0$–$C_{36}$ group; and v and y may be the same or different and are 0 or 1.

$R^3$, $R^4$ and $R^6$ are generally fatty acids, alcohols or glycerides and $R^7$, $R^8$, $R^9$ and $R^{10}$ are generally fatty substituents (the carbon chain portion) of these molecules. Fatty acids of the general Formula IV fatty alcohols of the general Formula VI and glycerides, which can be monoglycerides or diglycerides of the general Formula V can be pure, substantially pure (less than 10% of another fatty species, or a mixture of two or more fatty species. Artificially created mixtures including, without limitation gadoleic (C20:1), erucic (C22:1), arachadonic (C20:4) and culpodonic (C22:5) could be used as well. Fatty substituents may be provided from fatty acid containing oils, triglycerides, which can be converted to produce mono and diglycerides of the Formula V, and as fatty acids, fatty alcohols, esters or salts. Indeed, fatty acid materials useful in accordance with the present invention can come from natural or synthetic sources and include pure fatty acids, fatty mixtures, triglycerides, oils, and waxes such as, for example, jojoba oil (fatty acids and fatty alcohols)

Often, the mixtures of fatty acids or fatty substituents useful for $R^3$, $R^4$ and $R^6$–$R^{10}$ can be composed of not only different fatty acid chain lengths and saturation, but also fatty acids with structural differences like ante-iso and iso fatty acids as well. One mixture that can be used is shown in Table I.

TABLE I

| Carbon Chain | Ante-iso Acids(%) | Normal Acids (%) | Iso-Acids |
|---|---|---|---|
| $C_{8-15}$ | <5 | <5 | <5 |
| $C_{16}$ | 0–10 | 0.1–20 | 0.1–20 |
| $C_{17}$ | 0–5 | 0–5 | 0.1–10 |
| $C_{18}$ | 0–10 | 0.1–20 | 0.1–20 |
| $C_{19}$ | 0–50 | 0–10 | 0–10 |
| $C_{20}$ | 0–5 | 0–10 | 1–40 |
| $C_{21}$ | 0–95 | 0–5 | 0–5 |
| $C_{22}$ | 0–5 | 0–10 | 1–20 |
| $C_{23}$ | 0–25 | 0–5 | 0–10 |
| $C_{24}$ | 0–5 | 1–15 | 1–20 |
| $C_{25}$ | 0–30 | 0.1–10 | 0.1–10 |

TABLE I-continued

| Carbon Chain | Ante-iso Acids(%) | Normal Acids (%) | Iso-Acids |
|---|---|---|---|
| $C_{26}$ | 0–5 | 0.1–10 | 0.1–20 |
| $C_{27}$ | 0–10 | 0–5 | 0–5 |
| TOTAL | 8–95 | 1.5–50 | 3.5–60 |

A more preferred fatty acid mixture useful to produce diester quats in accordance with the present invention has a fatty acid content distribution as shown in Table II below.

TABLE II

| Carbon Chain | Ante-iso Acids(%) | Normal Acids(%) | Iso-Acids (%) |
|---|---|---|---|
| $C_{8-15}$ | <3 | <3 | <3 |
| $C_{16}$ | 1–5 | 0.2–10 | 0.2–10 |
| $C_{17}$ | 0–3 | 0–3 | 0.2–5 |
| $C_{18}$ | 1–5 | 0.2–10 | 0.2–10 |
| $C_{19}$ | 4–25 | 1–5 | 1–5 |
| $C_{20}$ | 0–3 | 1–5 | 2–10 |
| $C_{21}$ | 7–50 | 0–3 | 0–3 |
| $C_{22}$ | 0–3 | 1–5 | 2–10 |
| $C_{23}$ | 2–15 | 0–3 | 1–5 |
| $C_{24}$ | 0–3 | 2–10 | 2–10 |
| $C_{25}$ | 2–20 | 0.2–5 | 0.2–5 |
| $C_{26}$ | 0–3 | 0.2–5 | 1–10 |
| $C_{27}$ | 0–10 | 0–5 | 0–5 |
| TOTAL | 15–75 | 10–50 | 10–50 |

$R^3$, and indeed $R^4$ and $R^6$ are typically fatty acid mixtures found in commercial lanolin, also known as lanolin acids. Of course, they can be mixtures of fatty alcohols of the same content and proportion depending again upon whether the amine ends in an acid or hydroxy group. Recall that in each instance, esters must be formed. A typical distribution of the fatty acids contained in lanolin acids is shown in Table III below.

TABLE III

| Carbon Chain | Ante-iso Acids (%) | Normal Acids (%) | Iso-Acids | Hydroxy-Acids (%) | Iso-Hydroxy Acids (%) |
|---|---|---|---|---|---|
| $C_{10}$ | 0 | 0.27 | 0.31 | 0 | 0 |
| $C_{11}$ | 0.80 | 0 | 0 | 0 | 0 |
| $C_{12}$ | 0 | 0.29 | 0.92 | 0 | 0 |
| $C_{13}$ | 0 | 0 | 1.20 | 0 | 0 |
| $C_{14}$ | 0 | 1.51 | 1.93 | 2.0 | 0.23 |
| $C_{15}$ | 3.07 | 0.47 | 0.31 | 0.91 | 0.54 |
| $C_{16}$ | 0.30 | 2.73 | 2.19 | 20.77 | 0.82 |
| $C_{17}$ | 1.69 | 0 | 0.23 | 0.21 | 0 |
| $C_{18}$ | 0 | 1.58 | 2.37 | 1.41 | 6.97 |
| $C_{19}$ | 4.30 | 0 | 0 | 0.76 | 0 |
| $C_{20}$ | 0 | 0.80 | 4.0 | 0.42 | 0 |
| $C_{21}$ | 3.81 | 0 | 0 | 0 | 0 |
| $C_{22}$ | 0 | 0.77 | 1.99 | 0.25 | 0 |
| $C_{23}$ | 1.28 | 0 | 0 | 0 | 0 |
| $C_{24}$ | 0 | 2.42 | 1.95 | 0 | 0 |
| $C_{25}$ | 0 | 0 | 3.23 | 0 | 0 |
| $C_{26}$ | 0 | 1.08 | 2.0 | 0 | 0 |
| $C_{27}$ | 1.22 | 0 | 0 | 0 | 0 |
| TOTAL | 17.67 | 12.87 | 21.43 | 26.73 | 8.56 |

Ante-iso acids conform to the following formula:

where "z" can be any positive whole number, and R is an alkyl group, substituted or un-substituted, straight chain or branched, saturated or unsaturated. This alkyl group may be substituted or unsubstituted.

Hydroxy fatty acids include at least one —OH group attached to the fatty acid chain. Iso fatty acids are similar to ante-iso fatty acids except that the attached alkyl group is located closer to the carbonyl group, usually on the next adjacent carbon. Hydroxy fatty alcohols are also contemplated.

Fatty acids, alcohols and glycerides useful for $R^3$, $R^4$ and $R^6$–$R^{10}$ are generally often derived from, or can be created from, naturally occurring and artificially created oils. Oils, in accordance with the present invention include, without limitation, HEAR oil, as well as cod liver oil, herring oil, menhaden oil, mustard seed oil, pilchard oil, HEAR oil, salmon oil, sardine oil, meadowfoam oil and shark liver oil. The C-20+components of some of these oils are as follows: Cod liver oil—8.8–14.6% Eicosenoic acid (C20:1), 2.6–9% Eicosapentaenoic acid (C20:5), 4.6–13.3% Docosenoic (Erucic) acid (C22:1), 1–2% Docosapentaenoic acid (C22:5) and 8.6–19% Docosahexaenoic acid (C22:6); Herring oil—1.5–19.2% Eicosenoic acid (C20:1), 4.6–10.2% Eicosapentaenoic acid (C20:5), 2.8–19.9% Docosenoic (Erucic) acid (C22:1), 1–3.7% Docosapentaenoic acid (C22:5) and 3.8–24.1% Docosahexaenoic acid (C22:6); Menhaden oil—0.9–2.7% Eicosenoic acid (C20:1), 0.6–1.2% Eicosatetraenoic acid (C20:4), 10.2–13.5% Eicosapentaenoic acid (C20:5), 0.7–1.7% Docosenoic (Erucic) acid (C22:1), 1.1–2.3% Docosapentaenoic acid (C22:5) and 3.3–14% Docosahexaenoic acid (C22:6); Pilchard (Sardine) oil—3.2% Eicosenoic acid (C20:1), 1.6% Eicosatetraenoic acid (C20:4), 16.9% Eicosapentaenoic acid (C20:5), 3.6% Docosenoic (Erucic) acid (C22:1), 2.5% Docosapentaenoic acid (C22:5) and 12.9% Docosahexaenoic acid (C22:6); HEAR oil—0.8–13.5% Eicosenoic acid (C20:1), 20.1–59.4% Docosenoic (Erucic) acid (C22:1), 0.1–1.4% Tetrcosanoic (C24:0); Mustard Seed oil —7% Eicosenoic acid (C20:1), 44.2% Docosenoic (Erucic) acid (C22:1). Oils rich in Tetracosaenoic (Nervonic) acid (C24:1) such as genetically altered HEAR oil also work well. Of course, variations in content can occur. See generally 1 "Bailey's Industrial Oil and Fat Products" (Daniel Swern, John Wiley & Sons, 4th Ed. 1979) pp. 416, 417, 447, 449, 450 and 452, all of which are attached and hereby incorporated by reference.

Each of the foregoing oils has a distribution of fatty acids (usually in the form of trigylcerides), which includes preferably at least 30% of a C-20 or greater component and such long chain fatty substituents are preferred. Fatty acids, alcohols and mono and diglycerides can be derived from these or other triglycerides.

UV protecting groups include a UV-active moiety. A group of atoms or a portion of a molecule qualifies as a UV-active moiety if such group of atoms or portion of a molecule is capable of absorbing or blocking electromagnetic waves in ultraviolet region of electromagnetic spectra. For example, a UV protecting group may be any organic moiety that possesses quantized levels of molecular energy suitable for excitation in the UV spectral region. Also, chemical compounds that contain such organic moieties, for example, may be observed in the dark upon irradiation of such compounds by UV radiation. Especially useful moieties absorb electromagnetic radiation in UVA and/or UVB spectral regions. UV protecting groups can end in an acid or alcohol. If they are to be attached as $R^3$, $R^4$ or $R^6$ to an alkoxylated amine, then they will be in the form of an acid having a reactive carboxyl group for creating an ester. If they are to be attached as $R^3$, $R^4$ or $R^6$ to a diacid or triacid, which is itself bound to the alkoxylated amine, then it should have a reactive alcohol or hydroxy group. Of course, these acid forms could also be used to attach to the di-, triacid groups, however, a bridge such as a diol will be required.

In contrast to many known sunscreen agents, the diester quats of the invention have good adhesion to hair, and thus remain on the hair to performing its sunscreen function. At the same time, these compounds may still be used as active hair conditioning ingredients in products and formulations that are not intended for sun protection purposes.

Preferably, the UV-protecting group includes groups of atoms or portion(s) of a molecule that has/have multiple bonds (e.g., double and/or triple bonds) and/or aromatic systems, both conjugated and non-conjugated in various combinations. Preferred examples include aminobenzoate system

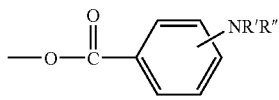

where examples of R' and R" include hydrogen, methyl, methoxy, ethyl, and other groups known to as part of the aminobenzoate system in conventional UV-absorbing compounds, and —NR'R' is preferably in para position, and cinnamate system

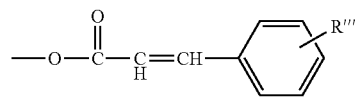

where examples of R'" include hydrogen, methyl, methoxy, and other groups known to as part of the cinnamate system in conventional UV-absorbing compounds. Particularly preferred examples include para-aminobenzoate system and cinnamate system These groups of atoms are arranged in a manner that provides conjugated multiple bonds and aromatic ring. While the invention is not limited to any particular theory, it is believed that such conjugation may contribute UV absorption/blocking ability.

Preferably, the UV protecting group includes a group or groups derived from compounds suitable for use as sun protection ingredients in cosmetic and/or personal care products. Non-limiting examples of such compounds include para-aminobenzoic acid (PABA), dimethyl PABA, benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, avobenzone, and 2,6-dicarboxynaphtalenic acid.

Poly fatty acids are preferably hydrophobic in nature and are often produced by reacting the acid groups of fatty acids with hydroxy group substitutions on their fatty substituents. These poly fatty acids can terminate in an alcohol or acid as may be needed for attachment to a diester quat of the present invention. Substituted or unsubstituted (but at least substituted with a hydroxy group) fatty alcohols and fatty acids having between 4 and 36 carbons including, for example, lactic acid, isostearic, hydroxy stearic and ricinoleic acids, and derivatives thereof may be used to produce poly fatty acids such as those having the structures:

and:

-continued

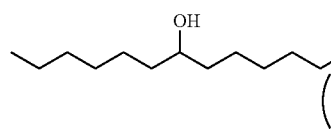 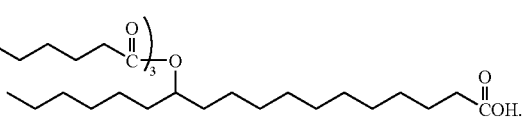

While both of these include a total of 5 units, the number of units can range from 2 to 15 units. Moreover, it is possible to make hybrids that are combinations of, for example, different hydroxy fatty acids or different fatty acids and fatty alcohols, etc. Again, when these are used for $R^3$, $R^4$, or $R^6$, if the alkoxylated amine ends in OH or O—, the poly fatty acids will end in a reactive carboxylic group—they will end in acids. If the alkoxylated amine is reacted with di or triacids, the poly fatty acids will end in a reactive alcohol or hydroxy group. Poly fatty acids can be reacted with acid groups by using a diol.

When v or y equals 0, $R^3$ and/or $R^4$ respectively as appropriate may be Formula IV

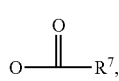

Formula IV a UV protecting group ending in a carboxylic acid or a poly fatty acid ending in a carboxylic acid. $R^7$, UV protecting groups and poly fatty acids are as previously defined.

When v equals 1, $R^3$ may be Formula V, VI

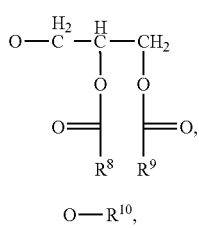

Formula V

Formula VI a UV protecting group ending in a hydroxy or alcohol group or a poly fatty acid ending in a hydroxy or alcohol group. $R^8$, $R^9$ and $R^{10}$ are the same or different, branched or straight chain, substituted or unsubstituted, saturated or unsaturated alkyl, cyclic or aromatic groups $C_1$ to $C_{36}$ in total carbon atoms and were defined previously as were the UV protecting group and poly fatty acids.

When y equals 1, $R^4$ may be Formula V, VI

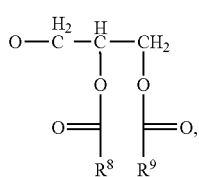

Formula V

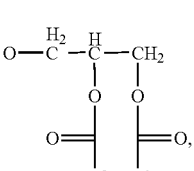

Formula VI a UV protecting group ending in a hydroxy or alcohol group or a poly fatty acid ending in a hydroxy or alcohol group. $R^8$, $R^9$ and $R^{10}$ are the same or different, branched or straight chain, substituted or unsubstituted, saturated or unsaturated alkyl, cyclic or aromatic groups $C_1$ to $C_{36}$ in total carbon atoms and were defined previously as were the UV protecting groups and poly fatty acids.

When v or y is 1 and B or F are Formula III, $R^6$ is Formula V, VI

Formula V

Formula VI a UV protecting group ending in a hydroxy or alcohol group or a poly fatty acid ending in a hydroxy or alcohol group. $R^8$, $R^9$ and $R^{10}$ are the same or different, branched or straight chain, substituted or unsubstituted, saturated or unsaturated alkyl, cyclic or aromatic groups $C_1$ to $C_{36}$ in total carbon atoms and were defined previously as were the UV protecting groups and poly fatty acids. Of course, as to all of the foregoing, bridging molecules such as diols, can be used to connect Formula IV to amines where x or y is 1.

The diester quats of Formula I are generally positively charged and are usually, but not always associated with a counter ion Z. These include, without limitation, halogens, alkyl sulfates and anything else known to be useful as a counter ion for quats. This can include, for example, the use of additional fatty acid species such as lactates to form a cation ion salt.

The at least one personal care ingredient can include, without limitation, any solvent, surfactant, conditioner, pigment, UV protector, color, fragrance, dye, excipient or additive useful in formulating personal care products such as, without limitation, cosmetics, sun-screens and sun-blocks, shampoos, conditioners, softeners and the like.

Particularly preferred are those personal care products having a pH which ranges from between about 4.0 to about 10.0, more preferably about 5.0 to about 9.0, even more preferably about 5.5 to about 8.5 and yet, even more preferably from about 6 to about 8. A particularly preferred diester quat useful in accordance with the present invention has the Formula VII.

Formula VII

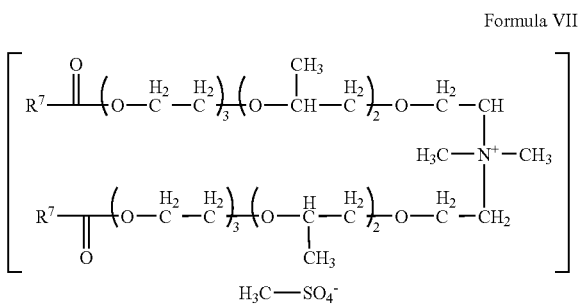

In Formula VII, the two $R^7$ groups, one part of $R^3$ and the other part of $R^4$ are preferably a mixture of fatty substituents derived from using lanolin fatty acids. With reference to Formula I, in Formula VII, A and E are identical as are u and x. In fact, u and x are each 5 with three of the A units being ethoxy groups and two being branched propoxy groups. The same is true for E. Both $R^1$ and $R^2$ are methyl groups and both v and y are zero so that there are no groups of B or F.

By way of another, non-limiting example consider the structure of Formula VIII:

Formula VIII

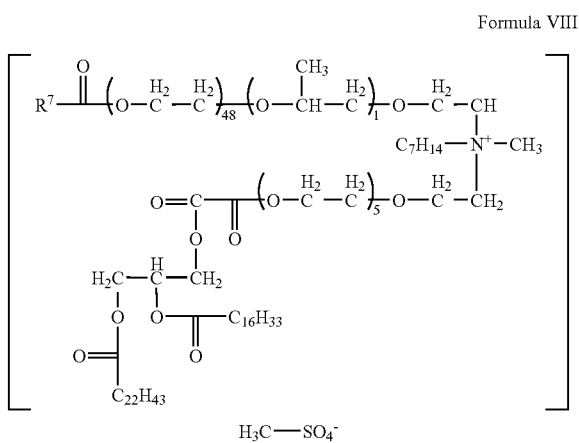

In Formula VIII, $R^1$ is $CH_3$—, $R^2$ is $C_7H_{14}$—, $R^4$ is a group of Formula V where $R^8$ is a fatty acid based group which is saturated and has 12 carbons and $R^9$ is an unsaturated fatty acid group of 22 carbons in length. $R^7$ is a mixture of fatty groups or fatty substituents of various length and proportion produced by using lanolin fatty acids. A includes one propoxy group and 48 ethoxy groups, u is 49 and v is zero. E is composed entirely of ethoxy units and x is 5. F has the structure of Formula II, G is $C_0$, and y is 1

The preparation of diester quats of the invention may be carried out by well known methods. Condensation reactions are predominant. Schematically, however, an alkyl diethanol amine can be reacted with various proportions of alkoxylating compounds to produce alkoxylated amine species. The amount and order of addition of these alkoxylating species will determine their relative arrangement and proportion. For example, if in Step 1AA, M moles is 10, then the resulting compound will be symmetrical and with u and x both being 5 and A and E being five consecutive ethoxy groups each. If the next reactant added is N Moles, which is 2, then the sixth alkoxy group for each side will be propoxy. It will be appreciated that variations can occur and therefore it is possible that the result will be a mixture that is neither symmetric nor in the desired order. However, generally, the predominant fraction of all of the alkoxylated amines produced will be the desired structure. These can be separated to isolate the amine of the desired structure. The reaction can proceed as illustrated in 1AA.

STEP 1AA

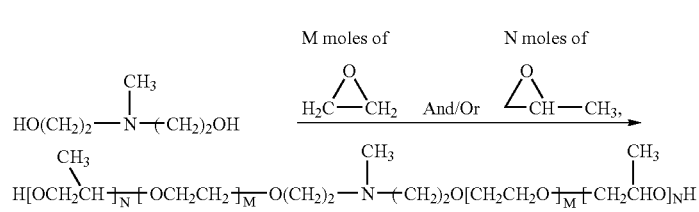

The alkoxylated material of Step 1AA can then be reacted with a di- or triacid or with a one of the other groups discussed herein for $R^3$ or $R^4$. If an acid is used, the resulting intermediate is then reacted with one of the other groups discussed herein for $R^3$, $R^4$ and possibly $R^6$ Alternatively, it may be desirable to produce various chains of alkoxy groups separately and then react them either with a fatty acid, fatty alcohol, glyceride or an alkyl diethanol amine. This allows one to tailor the specific chain length and order of the alkoxy groups more precisely. Indeed, separations can be performed to eliminate mixtures as the chain length grows. Alternatively, a fatty acid or fatty alcohol can be alkoxylated (in the case of a fatty alcohol, a bridging diacid or triacid may be necessary) and the resulting molecule then reacted with the alkyl diethanol amine to produce compounds like those found in Formula I. However, obviously, these compounds are tertiary amines until they have been quaternized.

Lastly, quats are formed. This is preferably done after the diester tertiary amines are completely formed. After the fatty acids, for example, are reacted with the alkoxylated amine, the resulting diester tertiary amines are then quaternized using known techniques with any suitable alkylating agent that can provide the appropriate $R^1$ or $R^2$ group. These can include methyl chloride, ethyl chloride, benzyl chloride, behyneal halide, dimethyl sulfate, diethyl sulfate, etc.

The viscosity of the personal care products in accordance with the present invention ranges from about 100–300,000 cps, more preferably about 500–300,000 cps, most preferably from about 1,000–300,000 cps. The amount of the diester quats in accordance with the invention found in the resulting personal care product generally range from about 0.1 to about 20% on a cationic actives or cationic activity basis. More preferably, the amount is between about 0.5 to about 15%, more preferably about 1% to about 10% on a cationic activity basis. Most preferred, the amount of diester quats of the invention in personal care products will range from between about 1 to about 5% based on a cationic activity basis.

Cationic activity may be measured by several methods readily understood by those skilled in the art. One such method utilizes a standardized solution of an anionic material, such as sodium lauryl sulfate. This material is added to the solution containing the quat until full complexation of the quat's cations (the end point) has been reached. The end point can be measured potentiometrically or by the use of color indicators.

Typical tests involve titrating a sample of the quat, usually dissolved in a solvent, with the standardized solution of sodium lauryl sulfate until the endpoint is reached. As described in the co-pending and co-assigned U.S. patent application Ser. No. 09/438,631, incorporated by reference herein in its entirety, once the endpoint is reached, the cationic activity can be calculated according to the following formula:

$$\% \text{ cationic activity} = \frac{mL \times N \times MW \times 100}{S.wt. \times 1000}$$

Where:
mL=the number of mL of anionic material
N=the normality of the solution used
MW=the equivalent molecular weight of the quat being analyzed
S.wt.=the sample weight in grams For additional information regarding the methodology for measuring the cationic activity, see W. Schempp and H. T. Trau, *Wochenblatt fur Papierfabrikation* 19, 1981, pp. 726–732, or J. P. Fischer and K. Lohr, *Organic Coatings Science Technology*, Volume 8, pp. 227–249, Marcel Dekker, Inc. April 1986), both incorporated herein by reference in their entirety.

It is also generally appropriate to describe the amount of claimed materials using other terminology. It is unusual for diesters to be produced or sold in a completely pure form. Whether singular compounds or as parts of mixtures, they generally are present as liquids or solids, which are including a solvent which, preferably, acts as a carrier. Because it is possible to drive off all, or substantially all, of the solvent, the upper limit on the proportion of diesters is generally less critical. However, when mixed in a solvent, the diester quats and the diester tertiary amines (if not formed into quats) should be present in the resulting solutions in an amount of at least about 0.10% by weight of the solution, more preferably at least about 5% by weight of the solution and most preferably at least about 20% by weight of the solution. If solvent or carrier is present, the diesters, quats or amines may be present in as much as about 99.0%. More typically, it is present in amounts of up to about 95% and even more typically in amounts of about 75% or less. An effective amount of the solvent or carrier in this context is an amount sufficient to solubilize the diesters, tertiary amines or quats, understanding that they can be in the form of solid solutions or other forms which can be flakable which may provide for more convenient handling. Solvents for flakable quats would often include free fatty alcohols as a cosolvent. This generally means that the amount of solvent in a diester containing additive product ranges from between about 1% to about 99.9%, or preferably between about 5% to about 95% by weight. More typically, however, 80% or less of the formulation is solvent. Most preferably, the amount of solvent is, however, minimized.

When diester quat additives (with or without solvent or carriers) are used to formulate personal care products, the amount used will vary depending upon a number of factors none the least of which is the overall diester quat molecule, the end product and the role that the diester quat will play. If the diester quat is merely being used for conditioning, one amount may be necessary. If the diester quat is also being used to provide UV protection, some other amount may be indicated. Moreover, depending upon the concentration of the diester quat in the additive to be used, the overall amount of additive may need to be adjusted. The same volume of additive which contains 20% solvent and one which contains 80% solvent obviously affords significantly different quantities of diester quat. This is why the amount is often expressed in terms of cationic activity. The amount of quat containing additive used in each case may be dramatically different although the intended amount of diester quat used may be the same. Furthermore, there is generally no upper limit on the amount of diester quat used. Usually cost is the only limiting factor. Of course, at some point the amount of diester quat used may produce a diminishing return. The lower limit is often more critical. Generally, at least about 0.05% by weight of the finished formulation (shampoo, conditioner, sunscreen, cosmetic, etc.) will be an diester quat or mixture as defined herein. More preferably at least about 0.5% by weight of diester quat of the present invention will be used and more preferably at least about 1% of the diester quat, by weight can be used. Generally, not more than about 50% of the formulation by weight and more preferably not more than 25% by weight of the formulation will be a diester quat of the present invention.

It is desirable to provide diester quats in a concentrated form with high cationic activity, as a solid or semi-solid solution or dispersion. Without wishing to be bound by any specific theory, it is believed that a desired amount of a given quat or mixture of quats to be placed in a formulation may be measured by the cationic activity of the quat raw material. Diester quat raw materials with high cationic activity permit better transportation efficiency since they occupy smaller space while providing the same desired quat amounts. It is also desirable to produce raw quats that, in addition to having high cationic activity, provide for ease in commercial handling and storage. For example, the raw quat that melt at lower temperatures minimize quat decomposition and improve energy efficiency. For this purpose, it is preferred for the raw quats to be flakable or pastillatable.

Thus, the invention also provides compositions containing diester quats and mixtures of diester quats, as well as mixtures of diester quats with other conventional active materials and additives. It is possible to mix diester quat diesters and diester quats and conventional esters and or quats, in the form of concentrated, often solid, solutions or suspensions in a suitable carrier. This is more likely, however for mixtures of diester quats and non-diester quats, with or without solvents or carriers. The preferred carrier or solvent is one that is or cosmetically acceptable and used or recognized to have such uses. Preferred solvents include isopropyl alcohol, SDA-40, propylene glycol, butylene glycol, various fatty alcohols, and mixtures thereof. In such instances, the combination of the carrier and the diester quats may be referred to as an additive and the diester quats may be present in an amount of from about 0.1% to about 99% of the additive by weight.

In accordance with another aspect, the invention also provides compositions in the form of various, personal care products which include one or more of the diester quats of the present invention. Such compositions may be cosmetics, sunscreen compositions for hair and/or skin, such as lotions, gels, sprays, creams and the like, hand cleaners, bath compositions, suntan oils, antiperspirant compositions, perfumes and colognes, cold creams, pre-shaves, deodorants, pharmaceutical preparations (ointments, creams, lotions, gels, treated powders, nose sprays, additives to bandages or transdermal drug applicators such as patches), skin moisturizers, facial cleansers, cleansing creams, skin gels, shampoos, hair conditioners (both conditioners which are rinsed and those which remain on the hair), rinses, cream rinses, detergents, make-up products, permanent waving products, lipsticks, mascara, blush, foundation, rouge, mousse, sprays, styling gels, nail care products including polish and nail conditioners and dyes and hair coloring products. The preferred final product compositions of the invention are compositions for treating human hair, such as shampoos or conditioners.

The nature of final products in accordance with the invention dictates a number of parameters including, amongst others, the type of diester quat to be used, whether a single type of diester quat is used or whether it is mixed with other diester quats of the present invention or other quats of other types, the amount of diester quats in accordance with the present invention which will be used, and the type and amount of additional ingredients. For example, in a topical skin conditioner, it may be desirable to omit coloring agents. However, in a hair dye, a nail polish or a blush, for example, pigments, dyes or colors, or materials which will develop color at some point in time during or after application may be specifically contemplated. The type and amount of pigment in a hair dye may be very different than the type and amount of pigment in a blush.

Personal care products in accordance with the present invention generally include a diester quat of the present invention, often in an acceptable solvent; said diester quat being present in the amount of from about 0.01% to 99.0% by weight based on the combine weight of said diester quat and a solvent; and at least one additional personal care ingredient, provided in an amount which is effective for its intended use. Of course, the solvent may be omitted. Those of ordinary skill in the art can readily substitute the diester quats of the present invention into existing formulations in an amount that approximates the use of functionally analogous compounds in existing formulations of the same type and function. For example, in a conditioning shampoo, diester quat formulations of the present invention may be substituted for some or all of the conditioning agents previously included. However, the personal care ingredient in this instance is the surfactants used for shampooing hair. Therefore, an amount of surfactants must be provided to meet that "intended use" in this case. If, in a given formulation, insufficient conditioning is obtained by a one to one substitution of the diester quats of the invention for conventional conditioners, then it is a relatively easy and conventional to determine the amount of diester quats necessary to provide sufficient additional conditioning using conventional techniques. Similarly, if one of the objects or "intended uses" of the formulation is to act as a sunscreen product for skin or hair, and a diester quat produced using a derivative of a UV-active compound as one of the groups bound is used as a UV absorbing agent, then the amount to be used will be that amount which imparts the desired skin protection factor or "SPF". If UV protection were to provided by a mixture of such diester quats with or without conventional UV absorbing quats, then the amount of each component will be such that in total, they provide the formulation with the desired SPF.

How much of each used to provide the desired level of SPF will be dictated not only by the resulting SPF but also by the relative cost of each, their relative availability, ease of formulation, other advantageous properties they may impart (i.e. one of the diester quats are also a particularly good conditioner and conditioning is desirable), and the like. In this instance, the personal care ingredient might be a conventional UV absorbing material or a cream, lotion or gel base and the effective amount would either be that which is required to provide some SPF factor or to form a cream, gel or lotion useful as a personal care product that successfully and stably supports the diester quats of the invention.

Personal care products in accordance with the present invention, which include one or more of the diester quats of the present invention, will generally include between about 0.05% and about 50% by weight of the diester quats of the invention. More preferably, the amount of diester quats will range from between about 0.5% to about 50% and even more preferably from between about 1% to about 25% by weight of the finished product. However, it will be appreciated that different amounts of the diester quats may be preferred given a particular product type.

Personal care products including the diester quats or mixtures thereof in accordance with the present invention may be in the form of liquids, ointments, lotions, sprays, gels, creams, emulsions, foams, pastes and solids; may be clear or opaque; and may be formulated as aqueous and non-aqueous preparations, including but not limited to topical preparations. Preferably, such final products are dispersions or solutions in water, or in a mixture of water with a suitable secondary solvent. Suitable solvents include various lower alkanols and glycols. Lower alkanols having from one to four carbon atoms are suitable for use with the present invention, and lower alkanols having from two to three carbon atoms are preferred. Glycols having from three to eight carbon atoms are suitable for use with the present invention, while glycols having from three to six carbon atoms are preferred. Examples of suitable lower alkanols and glycols include methanol, ethanol, isopropanol, butanol, hexylene glycol, 1,3-butylene glycol, 1,2- and 1,3-propane diol, 2-methyl 1,3-propane diol, propylene glycol, diethylene glycol, and the like.

The total amount of solvent, including water and mixtures of water and solvents, may be up to about 98% by weight of the composition, preferably, from about 20% to about 90%, more preferably, from about 50% to about 90% by weight of the composition. Again, however, different amounts of solvent may be preferred depending on the nature of the product. If a mixture of water and a secondary solvent is used, the secondary solvent may be present in the amount of up to 90%, preferably, between about 25% and about 80% by weight of water in the composition.

In addition to diester quats, the formulations of the invention may include various personal care ingredients, both conventional and otherwise. Of course, a decision to include an ingredient and the choice of specific ingredients depends on the specific application and product formulation.

Such personal care ingredients may include one or more substances such as cleaning agents, hair conditioning agents, skin conditioning agents, hair styling agents, antidandruff agents, hair growth promoters, perfumes, sunscreen compounds, pigments, moisturizers, film formers, humectants, alpha-hydroxy acids, hair colors, make-up agents, detergents, thickening agents, emulsifiers, antiseptic agents, deodorant actives and surfactants. They may include agents which enhance permeation into or through the skin, or topical pharmaceuticals such as, without limitation, corticosteriods, analgesics, anti-inflammatory agents, antibiotics, anesthetics, etc. These may all be used in conventional and/or approved amounts.

Personal care ingredients generally can be included in various forms. They may be included in a liquid or solid form. Solids can be crystalline or amorphous, granular, powder, particulate and the like. However, it is also possible for such additives to be microencapsulated or in the form of micro particles.

One of the personal care ingredients which may be used in products along with the diester quats of the present invention are surfactants including one or more nonionic surfactants, anionic surfactants, cationic surfactants, amphoteric surfactants, zwitterionic surfactants, and mixtures thereof. Surfactants in cleansers or shampoos could be an active agent. In other formulations, it can be an emulsifier and is, therefore, an additional agent. For some of surfactants that may be used in combination with the compositions of the invention, see McCutcheon's, *Detergents and Emulsifiers*, (1986), as well as U.S. Pat. Nos. 5,151,210, 5,151,209, 5,120,532, 5,011,681, 4,788,006, 4,741,855, 4,704,272, 4,557,853, 4,421,769, and 3,755,560; all incorporated herein by reference in their entirety.

Cationic surfactants suitable for use in various personal care products, especially hair care products such as conditioners and shampoos include quaternary ammonium cationic surfactants of the formula

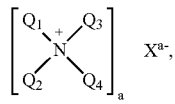

where X and a are as previously described, $Q_1$ is $C_{12}$–$C_{22}$ alkyl, $C_{12}$–$C_{22}$ alkyl amido $C_1$–$C_6$ alkylene, $C_{12}$–$C_{22}$ alkylhydroxy; $Q_2$ is $C_{12}$–$C_{22}$ alkyl, $C_{12}$–$C_{22}$ alkyl amido $C_1$–$C_6$ alkylene, $C_{12}$–$C_{22}$ alkylhydroxy, benzyl, or $C_1$–$C_6$ alkyl; $Q_3$ and $Q_4$ are independently $C_1$–$C_6$ alkyl or benzyl.

Examples of suitable quaternary ammonium surfactants include cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof.

Additional quaternary ammonium salts include those wherein the $C_{12}$–$C_{22}$ alkyl is derived from a tallow fatty acid or from a coconut fatty acid. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconut alkyl)dimethyl ammonium chloride, di(coconut alkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred quaternary ammonium surfactants are dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Fatty Amines

The compositions of the invention may also include salts of primary, secondary and tertiary $C_{12}$–$C_{22}$ amines. Examples of such suitable amines include stearamido propyl dimethyl amine, diethyl amino ethyl stearamide, dimethyl stearamine, dimethyl soyamine, soyamine, tri(decyl)amine, ethyl stearylamine, ethoxylated stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Some cationic amine surfactants useful in the compositions of the present invention are disclosed in U.S. Pat. No. 4,275,055, incorporated by reference herein.

Amidoamines

The compositions of the invention may also include amidoamines, such as disclosed in U.S. patent application Ser. No. 09/409,203, assigned to Croda Inc., and incorporated by reference herein. Suitable additional cationic surfactants are disclosed in McCutcheon, Detergents & Emulsifiers, (M.C. Publishing Co. 1979); U.S. Pat. Nos. 3,155,591, 3,929,678, 3,959,461, and 4,387,090, which are incorporated by reference herein. The amounts and the nature of cationic surfactants present in the compositions of the invention, if at all, depend on the nature of the composition. In the final product, the total amount of cationic surfactants, may vary from 0.1% to about 40%, more preferably, from about 0.1% to about 15%, yet more preferably, from about 0.5% to about 2% by the weight of the product composition. However, different amounts of cationic surfactants may be preferred depending on the nature of the product.

The compositions of the invention may also include various non-ionic surfactants. Among the suitable nonionic surfactants are condensation products of $C_8$–$C_{30}$ alcohols with sugar or starch polymers. These compounds can be represented by the formula $(S)_n$—O—R, wherein S is a sugar moiety such as glucose, fructose, mannose, and galactose; n is an integer of from about 1 to about 1000, and R is $C_8$–$C_{30}$ alkyl. Examples of suitable $C_8$–$C_{30}$ alcohols from which the R group may be derived include decyl alcohol, cetyl alcohol, stearyl alcohol, lauryl alcohol, myristyl alcohol, oleyl alcohol, and the like. Specific examples of these surfactants include decyl polyglucoside and lauryl polyglucoside.

Other suitable nonionic surfactants include the condensation products of alkylene oxides with fatty acids (i.e., alkylene oxide esters of fatty acids). These materials have the general formula $RCO(X)_n$ OH, wherein R is a $C_{10}$–$C_{30}$ alkyl, X is —$OCH_2CH_2$— (derived from ethylene oxide) or —$OCH_2CHCH_3$— (derived from propylene oxide), and n is an integer from about 1 to about 200.

Yet other suitable nonionic surfactants are the condensation products of alkylene oxides with fatty acids (i.e., alkylene oxide diesters of fatty acids) having the formula $RCO(X)_nOOCR$, wherein R is a $C_{10}$–$C_{30}$ alkyl, X is —$OCH_2CH_2$—(derived from ethylene oxide) or —$OCH_2CHCH_3$— (derived from propylene oxide), and n is an integer from about 1 to about 200.

Yet other nonionic surfactants are the condensation products of alkylene oxides with fatty alcohols (i.e., alkylene oxide ethers of fatty alcohols) having the general formula $R(X)_nOR'$, wherein R is $C_{10}$–$C_{30}$ alkyl, n is an integer from about 1 to about 200, and R' is H or a $C_{10}$–$C_{30}$ alkyl.

Still other nonionic surfactants are the compounds having the formula $RCO(X)_nOR'$ wherein R and R' are $C_{10}$–$C_{30}$ alkyl, X is —$OCH_2CH_2$— (derived from ethylene oxide) or —$OCH_2CHCH_3$— (derived from propylene oxide), and n is an integer from about 1 to about 200.

Examples of alkylene oxide-derived nonionic surfactants include ceteth-1, ceteth-2, ceteth-6, ceteth-10, ceteth-12, ceteraeth-2, ceteareth6, ceteareth-10, ceteareth-12, steareth-1, steareth-2, stearteth-6, steareth-10, steareth-12, PEG-2 stearate, PEG4 stearate, PEG6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amides disclosed, for example, in U.S. Pat. Nos. 2,965,576, 2,703,798, and 1,985,424, which are incorporated herein by reference.

If non-ionic surfactants are used, their amounts will vary based on the formulation, the remaining ingredients and the types, if any, of any surfactants which are being used. In general, the amount of non-ionic surfactants which are useful in accordance with the present invention may vary from 0.1% to about 40%, more preferably from about 0.1% to about 15%, and yet more preferably from about 0.5% to about 2% by weight of the final formulation. However, as previously noted, different amounts of non-ionic surfactants may be preferred, depending on the nature of the product.

The compositions of the invention may also include various anionic surfactants. Several examples of suitable anionic surfactants are disclosed in U.S. Pat. No. 3,929,678, which is incorporated herein by reference. Further examples of suitable anionic surfactants include alkoyl isethionates, and alkyl ether sulfates.

The alkoyl isethionates typically have the formula RCO—$OCH_2CH_2$—$SO_3M$, wherein R is $C_{10}$–$C_{30}$ alkyl, and M is a water-soluble cation, such as ammonium, sodium, potassium, or triethanolamine. The examples of suitable isethionates include ammonium cocoyl isethionate, sodium cocoyl isethionate, sodium lauroyl isethionate, sodium stearoyl isethionate, and mixtures thereof. Preferred for used herein are ammonium cocoyl isethiohate, sodium cocoyl isethionate, and mixtures thereof.

The alkyl ether sulfates typically have the formulas $ROSO_3M$ and $RO(C_2H_4O)_xSO_3M$, where R is $C_{10}$–$C_{30}$ alkyl, x varies from about 1 to about 10, and M is a water-soluble cation such as ammonium, sodium, potassium and triethanolamine.

Yet another suitable class of anionic surfactants are alkali metal salts of $C_8$–$C_{30}$ carboxylic acids and alkylsulfonates of the formula $R_1$—$SO_3M$ (where $R_1$ is $C_8$–$C_{30}$ alkyl; preferably, $C_{12}$–$C_{22}$ alkyl, and M is a cation), including succinamates, and $C_{12}$–$C_{24}$ olefin sulfonates and carboxylates.

If ionic surfactants are used, their amounts will vary based on the formulation, the remaining ingredients and the types, if any, of any surfactants which are being used. In general, the amount of ionic surfactants which are useful in accordance with the present invention may vary from 0.1% to about 40%, more preferably from about 0.1% to about 15%, and yet more preferably from about 0.5% to about 2% by weight of the final formulation. However, as previously noted, different amounts of ionic surfactants may be preferred, depending on the nature of the product.

The compositions of the invention may also include zwitterionic and amphoteric surfactants. Suitable amphoteric and zwitterionic surfactants are, for example, derivatives of mono- or di-$C_8$–$C_{24}$ secondary and tertiary amines, such as alkyl imino acetates, carboxylates, sulfonates, sulfates, phosphates, and phosphonates, including iminodialkanoates and aminoalkanoates of the formulas $RN(CH_2)_m CO_2 M_2$ and $RNH(CH_2)_m CO_2M$, where m varies from 1 to 4, R is $C_8$–$C_{30}$ alkyl; preferably, $C_{12}$–$C_{22}$ alkyl, and M is H, alkali metal, alkaline earth metal ammonium, or alkanolammonium.

Other suitable amphoteric and zwitterionic surfactants are imidazolinium and ammonium derivates. Suitable examples of such amphoteric surfactants include sodium 3-dodecylaminopropionate, sodium 3-dodecylaminopropane sulfonate, N-alkyltaurines; N-higher alkyl aspartic acids, and coamidopropyl PG-dimonium chloride phosphate. For further examples of suitable amphoteric and zwitterionic surfactants, please see U.S. Pat. Nos. 2,658,072, 2,438,091, and 2,528,378, which are incorporated herein by reference Yet other suitable amphoteric and zwitterionic surfactants are betaines. Examples of suitable betaines include coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines, oleyl betaine, and cocamidopropyl betaine.

The compositions of the invention may include quaternary ammonium compositions of matter of the formula

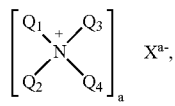

where X and a are as previously described, $Q_1$ is $C_{12}$–$C_{22}$ alkyl, $C_{12}$–$C_{22}$ alkyl amido $C_1$–$C_6$ alkylene, $C_{12}$–$C_{22}$ alkylhydroxy; $Q_2$ is $C_{12}$–$C_{22}$ alkyl, $C_{12}$–$C_{22}$ alkyl amido $C_1$-$C_6$ alkylene, $C_{12}$–$C_{22}$ alkylhydroxy, benzyl, or $C_1$–$C_6$ alkyl; $Q_3$ and $Q_4$ are independently $C_1$–$C_6$ alkyl or benzyl. These quats may be used alone or in combination with diester quat quats of the present invention. Thus, a formulation in accordance with the present invention could include an diester quat, an diester quat and a conventional quat as well.

Examples of suitable quaternary ammonium compounds include cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium chloride, distearyl methyl ammonium bromide, and mixtures thereof.

Additional quaternary ammonium salts include those wherein the $C_{12}$–$C_{22}$ alkyl is derived from a tallow fatty acid or from a coconut fatty acid. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconut alkyl)dimethyl ammonium chloride, di(coconut alkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred quaternary ammonium compositions are dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

When present, quaternary ammonium compositions (other than those made from diester quats) of the present invention can be provided in any amount desirable and the amount will depend upon the factors previously discussed, including the purpose of the end formulation and its overall composition. That said, however, these quaternary ammonium compositions may be present in an amount of between about 0 and about 50%, preferably in an amount of between about 0.1 and about 25% and more preferably in an amount of between about 1 and about 10% by weight of the final composition. These amounts may be reduced if quaternary ammonium compounds as described herein are used in combination with diester quats of the invention, although in certain circumstances, the presence of one will have no affect on the amount of the other used.

The compositions of the invention may also include salts of primary, secondary and tertiary $C_{12}$–$C_{22}$ amines. Examples of such suitable amines include stearamido propyl dimethyl amine, diethyl amino ethyl stearamide, dimethyl stearamine, dimethyl soyamine, soyamine, tri(decyl)amine, ethyl stearylamine, ethoxylated stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Some cationic amine surfactants useful in the compositions of the present invention are disclosed in U.S. Pat. No. 4,275,055, incorporated by reference herein.

The compositions of the invention may also include amidoamines, such as disclosed in U.S. patent application Ser. No. 09/409,203, assigned to Croda, Inc., and incorporated by reference herein. The amount of fatty amines and/or amidoamines will generally vary under the same conditions as the quaternary ammonium compounds as described above.

If amphoteric surfactants are used, their amounts will vary based on the formulation, the remaining ingredients and the types, if any, of any surfactants which are being used. In general, the amount of amphoteric surfactants which are useful in accordance with the present invention may vary from 0.1% to about 40%, more preferably from about 0.1% to about 15%, and yet more preferably from about 0.5% to about 2% by weight of the final formulation. However, as previously noted, different amounts of amphoteric surfactants may be preferred, depending on the nature of the product.

A wide variety of sunscreen compounds are suitable for use with the compositions of the present invention to provide UV protection. Depending on the nature of the composition, the sunscreen compounds may be added in the amount of up to about 40% by weight of the composition, preferably, from about 1% to about 30%. However, the preferred amount may vary depending on the nature of the composition. Thus, for the final product compositions in the form of a shampoo or conditioner, the suitable sunscreen agent may be included in the amount of up to about 40% by weight of the composition, preferably, from about 0.5% to about 10%, more preferably, from about 0.5% to about 5% by weight of the composition. This is exclusive of the amount of UV-protecting groups found in the diester quats used.

Sunscreens may be in the form of shampoos, conditioners including so-called "leave-in" conditioners, hairsprays, as well as products specifically intended as sunscreens for hair and/or skin including lotions, gels, sprays and the like.

Suitable sunscreen compounds include, for example, p-aminobenzoic acid, its salts and its derivatives; anthranilates; salicylates; cinnamic acid derivatives; dihydroxycinnamic acid derivatives; trihydroxycinnamic acid derivatives; hydrocarbons; dibenzalacetone and benzalacetophenone; naphtholsulfonates; dihydroxy-naphtholic acid and its salts; coumarin derivatives; diazoles; quinine salts; quinoline derivatives; hydroxy- or methoxy-substituted benzophenones; uric and vilouric acids; tannic acid and its derivatives; hydroquinone; amino benzoates, salicylates, ferrulic acid derivatives, phenylbenzimidazole sulfonic acids, benzophenone sulfonic acids, thioctic acids derivatives, oil-soluble cinnamates, and benzophenones. For other suitable sunscreen compounds, please see Segarin, et al., Cosmetics Science and Technology, Chapter VIII, pp. 189 et seq., incorporated herein by reference.

Specific suitable sunscreen compounds include 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl-4->bis(hydroxypropyl) !-aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylaminobenzoate, 2-phenylbenzimidazole-5-sulfonic acid, 2-(p-dimethyl-aminophenyl)-5-sulfonicbenzoxazoic acid, para-aminobenzoic acid, benzophenone-1, benzophenone-1, benzophenone-2, benzophenone-3, benzophenone-4, benzophenone-5, benzophenone-6, benzophenone-8, benzophenone-12, methoxycinnamate, avobenzone, ethyl dihydroxypropyl para-aminobenzoate, glyceryl para-aminobenzoate, methyl anthranilate, octocrylene, octyl dimethyl para-aminobenzoate, octyl methoxycinnamate, octyl salicylate, zinc oxide, titanium dioxide, and red petrolatum.

In one embodiment of the invention, the diester quats of the present invention, and even more preferably, the diester quats themselves include one or more UV protecting groups, are mixed or blended with other UV active compounds or formulations which include other UV active compounds. Non-limiting examples of these other UV active compounds include all of those noted above and, preferably para-aminobenzoic acid (PABA), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, avobenzone, and 2,6-dicarboxynaphtalenic acid. These may be used in the amounts previously described for other sunscreen additives discussed above.

The compositions of the invention may also include one or emollient compounds such as fats, waxes, lipids, silicones, hydrocarbons, fatty alcohols and a wide variety of solvent materials. The amount of the emollient depends on the application. For the final product compositions, emollients are included in the amount of up to 50% by weight of the composition, preferably, from about 0.1% to about 20%, and more preferably, from about 0.5% to about 10% by weight of the composition.

Examples of suitable emollients include $C_{8-30}$ alkyl esters of $C_{8-30}$ carboxylic acids; $C_{1-6}$ diol monoesters and diesters of $C_{8-30}$ carboxylic acids; monoglycerides, diglycerides, and triglycerides of $C_{8-30}$ carboxylic acids, cholesterol esters of $C_{8-30}$ carboxylic acids, cholesterol, and hydrocarbons. Examples of these materials include diisopropyl adipate, isopropyl myristate, isopropyl palmitate, ethylhexyl palmitate, isodecyl neopentanoate, $C_{12-15}$ alcohols benzoates, diethylhexyl maleate, PPG-14 butyl ether, PPG-2 myristyl ether propionate, cetyl ricinoleate, cholesterol stearate, cholesterol isosterate, cholesterol acetate, jojoba oil, cocoa butter, shea butter, lanolin, lanolin esters, mineral oil, petrolatum, and straight and branched $C_{16}$–$C_{30}$ hydrocarbons.

Also useful are straight and branched chain fatty $C_8$–$C_{30}$ alcohols, for example, stearyl alcohol, isostearyl alcohol, ethenyl alcohol, cetyl alcohol, isocetyl alcohol, and mixtures thereof. Examples of other suitable emollients are disclosed in U.S. Pat. No. 4,919,934; which is incorporated herein by reference in its entirety.

Other suitable emollients are various alkoxylated ethers, diethers, esters, diesters, and trimesters. Examples of suitable alkoxylated ethers include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof.

Examples of alkoxylated diethers include PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof. Preferred are those selected from the group consisting of PPG-10 1,4-butanediol diether, PPG-12 1,4-butanediol diether, PPG-10 1,6-hexandiol diether, and PPG-12 hexanediol diether, and mixtures thereof.

Examples of suitable alkoxylated diesters and trimesters are disclosed in U.S. Pat. Nos. 5,382,377, 5,455,025 and 5,597,555, assigned to Croda Inc., and incorporated herein by reference.

Suitable lipids include $C_8$–$C_{20}$ alcohol monosorbitan esters, $C_8$–$C_{20}$ alcohol sorbitan diesters, $C_8$–$C_{20}$ alcohol sorbitan triesters, $C_8$–$C_{20}$ alcohol sucrose monoesters, $C_8$–$C_{20}$ alcohol sucrose diesters, $C_8$–$C_{20}$ alcohol sucrose triesters, and $C_8$–$C_{20}$ fatty alcohol esters of $C_2$–$C_{62}$-hydroxy acids. Examples of specific suitable lipids are sorbitan diisostearate, sorbitan dioleate, sorbitan distearate, sorbitan isosotearate, sorbitan laurate, sorbitan oleate, sorbitan palmitate, sorbitan sesquioleate, sorbitan esquistearte, sorbitan stearate, sorbitan triiostearte, sorbitan trioleate, orbitan tristeate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof.

Other suitable emollients include mineral oil, petrolatum, cholesterol, dimethicone, dimethiconol, stearyl alcohol, cetyl alcohol, behenyl alcohol, diisopropyl adipate, isopropyl myristate, myristyl myristate, cetyl ricinoleate, sorbitan distearte, sorbitan dilaurate, sorbitan stearate, sorbitan laurate, sucrose laurate, sucrose dilaurate, sodium isostearyl lactylate, lauryl pidolate, sorbitan stearate, stearyl alcohol, cetyl alcohol, behenyl alcohol, PPG-14 butyl ether, PPG-15 stearyl ether, and mixtures thereof.

The compositions of the invention may also include various emulsifiers. In the final product compositions of the invention, emulsifiers may be included in the amount of up to about 10%, preferably, in the amount of from about 0.5% to about 5% by weight of the composition. The examples of suitable emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, polyethylene glycols, polypropyleneglyocis, and mixtures thereof.

The compositions of the invention may also include antidandruff agents. The examples of suitable antidandruff agents include zinc pyrithione, sulphur, and selenium sulfide.

The compositions of the invention may also include hair oxidizing/reducing agents. The examples of suitable hair oxidizing/reducing agents include hydrogen peroxide, perborate, thioglycolates and persulfate salts.

The compositions of the invention may also include various thickeners, such as cross-linked acrylates, nonionic polyacrylamides, xanthan gum, guar gum, gellan gum, and the like; polyalkyl siloxanes, polyaryl siloxanes, and aminosilicones. In the final product compositions of the invention, thickeners may be included in the amount of up to about 10%, preferably, in the amount of from about 0.2% to about 5% by weight of the composition.

The specific examples of the suitable thickening silicon compounds include polydimethylsiloxane, phenylsilicone, polydiethylsiloxane, and polymethylphenylsiloxane. Some of the suitable silicon compounds are described in European Patent Application EP 95,238 and U.S. Pat. No. 4,185,017, which are incorporated herein by reference. The compositions of the invention may also include silicone polymer materials, which provide both style retention and conditioning benefits to the hair. Such materials are described in U.S. Pat. No. 4,902,499, which is incorporated herein by reference.

The compositions of the invention may also include hydrolyzed animal protein hair conditioning agents. Croda Incorporated sells an example of a commercially available material under the trade name Crotein Q-RTM. Other examples include urea, glycerol, and propoxylated glycerols, including those described in U.S. Pat. No. 4,976,953, which is incorporated by reference herein.

The compositions of the invention may also include a hair setting agent to impart styling benefits upon application to hair. The hair setting polymers may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or nonionic. Examples of anionic monomers include unsaturated carboxylic acid monomers such as acrylic acid, methacrylic acid, maleic acid, maleic acid half ester, itaconic acid, fumeric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyl-trimethylammonium chloride and (meth)acryloxypropyl-triethylammonium bromide; amine derivatives of methacrylic acid or amine derivatives of methacrylamide derived from methacrylic acid or methacrylamide and a dialkylalkanolamine having $C_1$–$C_6$ alkyl groups such as dimethylaminoethyl (meth)acrylate, diethylaminoethyl (meth)acrylate, dimethylaminopropyl (meth)acrylate, or dimethylaminopropyl (meth)acrylamide.

Examples of the amphoteric monomers include zwitterionized derivatives of the aforementioned amine derivatives of (meth)acrylic acids or the amine derivatives of (meth) acrylamide such as dimethylaminoethyl (meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth) acrylic acid or (meth)acrylamide, as discussed above, modified with propanesultone.

Examples of nonionic monomers are acrylic or methacrylic acid esters of $C_1$–$C_{24}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene; chlorostyrene; vinyl esters such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, methoxy ethyl (meth)acrylate, butoxyethyl (meth)acrylate; allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl (meth)acrylate, n-butyl methacrylate, isobutyl methacrylate, 2-ethylhexyl methacrylate, methyl methacrylate, t-butylacrylate, t-butylmethacrylate, and mixtures thereof.

Examples of anionic hair styling polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of cationic hair styling polymers are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate.

The compositions of the invention may also include a wide range of miscellaneous ingredients. Some suitable miscellaneous ingredients commonly used in the cosmetic and personal care industry are described in *The CTFA Cosmetic Ingredient Handbook*, (2$^{nd}$ Ed., 1992), which is incorporated by reference herein. These ingredients will be used in amounts which are conventional.

Thus, the compositions of the invention may also include one or more absorbents, anti-acne agents, antiperspirants, anticaking agents, antifoaming agents, antimicrobial agents, antioxidants, antidandruff agents, astringents, binders, buffers, biological additives, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, humectants, keratolytics, opacifying agents, pH adjusters, preservatives, propellants, proteins, retinoids, reducing agents, sequestrants, skin bleaching agents, skin-conditioning agents (humectants, miscellaneous, and occlusive), skin soothing agents, skin healing agents, softeners, solubilizing agents, lubricants, penetrants, plasticizers, salts, essential oils, and vitamins. The amount of each if used can vary widely depending on the product. However, they are generally used in conventional amounts. So, for example, if shampoos generally use between about 0.1 and 5% by weight of a fragrance, that is the amount that will generally be used in shampoos formulated with one or more of the diester quats of the present invention. Generally however, the amount of each of these used will be less than 50% by weight and more preferably less than or equal to 25% by weight.

The examples of suitable pH adjusters include sodium hydroxide, triethanoleamine, and aminomethylpropanol, and mixtures thereof. If pH adjusters are present in a final product composition, the amount may vary from about 0.01% to about 5%, preferably, from about 0.1% to about 2% by weight of the composition. Most important is the fact that the pH which results is between about 4 and 10, or preferably 5 and 9.

The examples of suitable film formers include glycerin/diethylene glycol myrystate copolymer, glycerin/diethylene glycol adipate copolymer, ethyl ester of PVM/MA copolymer, PVP/dimethiconylacrylate/polycarbamyl/polyglycol ester, and mixtures thereof. If the film formers are present in the final product compositions, the amount may vary from about 0.1% to about 15.0% by weight of the composition, preferably, from about 0.1% to about 2.5% by weight of the composition.

The examples of suitable vitamins include tocopherol, tocopherol acetate, retinoic acid, retinol, and retinoids.

The examples of suitable anti-acne medicaments include resorcinol, sulfur, salicylic acid, erythromycin, zinc, and benzoyl peroxide.

The examples of suitable skin bleaching or lightening agents include hydroquinone, and kojic acid. The examples of suitable aesthetic components such as fragrances, pigments, colorings, and the like, include panthenol and derivatives (e.g., ethyl panthenol), aloe vera, pantothenic acid and its derivatives, clove oil, menthol, camphor, eucalyptus oil, eugenol, menthyl lactate, witch hazel distillate, allantoin, bisabolol, and dipotassium glycyrrhizinate.

EXAMPLE #1

Preparation of PPG-4 PEG-6
N-Methyldiethanolamine

To a clean, dry stirred tank pressure vessel with Nitrogen inlet was charged 482.08 g (4.05 moles) of N-Methyldiethanolamine, a catalytic amount (5.54 g) of 45% KOH and 0.92 g of NaBH$_4$ as a color preservative. The vessel was then purged with Nitrogen and heated to 110° C. Vacuum was applied for one hour to remove trace amounts of water, after which the temperature was raised to 130° C. Propylene Oxide in the amount of 939.88 g (16.18 moles) was added at such a rate so the pressure remained below 50 psig. After all Propylene Oxide was added, the batch was left to react to constant pressure for an additional 4 hours after which the temperature was raised to 160° C. Ethylene Oxide in the amount of 1069.02 g (24.26 moles) was added at such a rate so that the pressure stayed below 50 psig. After all Ethylene Oxide was added the batch was left to react for an additional hour after which the temperature was lowered to 110° C. and full vacuum was applied for one hour. The reaction mixture was cooled to 50° C. and the catalyst was neutralized with 5.61 g of 50% Hypophosphorous Acid. The resulting product was a clear amber liquid.

EXAMPLE #2

Preparation of PPG-4 PEG-6
N-Methyldiethanolamine Di-Lanolate

To a clean dry stirred tank pressure vessel with Nitrogen inlet and fitted with a distillation column was charged 1204.84 g (1.94 moles) of the Alkoxylate from example 1, 1290.28 g (3.68 moles) of Lanolic Acid (from Croda, Inc.) and a catalytic amount (6.25 g) of 50% Hypophosphorous Acid. The batch was heated to 220° C. under Nitrogen sparge and held for one hour after which 100 mm Hg of vacuum was applied. During vacuum, the batch was monitored by measuring the Acid Value. The reaction was considered complete when the Acid Value reached 3.1 mg KOH. The finished product was a viscous amber liquid.

EXAMPLE #3

Preparation of PPG-4 PEG-6
N-Methyldiethanolamine Dibehenate

To a clean dry stirred tank pressure vessel with Nitrogen inlet and fitted with a distillation column is charged 268.16 g (0.44 moles) of the Alkoxylate from example 1, 281.82 g (0.83 moles) of Behenic Acid and a catalytic amount (1.38 g) of 50% Hypophosphorous Acid. The batch is heated to 220° C. under Nitrogen sparge and held for one hour after which 100 mm Hg of vacuum is applied. During vacuum, the batch is monitored by measuring the Acid Value. The reaction is considered complete when the Acid Value is preferably less than 5 mg KOH.

EXAMPLE #4

Preparation of PPG-4 PEG-6
N-Methyldiethanolamine Di-18-Methyl Eicosanoate

To a clean dry stirred tank pressure vessel with Nitrogen inlet and fitted with a distillation column is charged 348.14 g (0.57 moles) of the Alkoxylate from example 1, 351.86 g (1.07 moles) of 18-MEA Acid (from Croda, Inc.) and a catalytic amount (1.75 g) of 50% Hypophosphorous Acid. The batch is heated to 220° C. under Nitrogen sparge and held for one hour after which 100 mm Hg of vacuum is applied. During vacuum, the batch is monitored by measuring the Acid Value. The reaction is considered complete when the Acid Value is preferably less than 5 mg KOH.

EXAMPLE #5

Methosulfate QUAT of PPG-4 PEG-6 N-Methyldiethanolamine Di-Lanolate

To a clean, dry four neck round bottom flask fitted with Nitrogen inlet, mechanical stirrer, reflux condenser, temperature probe and drop funnel was charged 2129.92 g (1.62 moles) of the diester from example 2 and 1377.93 g of Dipropylene Glycol as a diluent. The batch was heated to 50° C. and 163.70 g (1.30 moles) of Dimethyl Sulfate was added drop-wise to maintain a temperature below 55° C. After all Dimethyl Sulfate was added the batch was left to react for an additional hour after which the Base Value was checked. The reaction was considered complete when the Base Value was 5.36 mg KOH. The batch was then filtered to leave a QUAT at 60% activity.

Quaternization of examples 3 and 4 can also be accomplished as described in example 5.

EXAMPLE #6

Preparation of PPG-6 N-Methyldiethanolamine

To a clean, dry stirred tank pressure vessel with Nitrogen inlet is charged 637.03 g (5.35 moles) of N-Methyldiethanolamine, a catalytic amount (5.55 g) of 45% KOH and 1.00 g of NaBH$_4$ as a color preservative. The vessel is then purged with Nitrogen and heated to 110° C. Vacuum is applied for one hour to remove trace amounts of water, after which the temperature is raised to 130° C. Propylene Oxide in the amount of 1862.97 g (32.08 moles) is added at such a rate so the pressure remains below 50 psig. After all Propylene Oxide is added, the batch is left to react to constant pressure for an additional 4 hours after which the temperature is raised to 160° C. After two hours the temperature is lowered to 110° C. and full vacuum is applied for one hour. The reaction mixture is cooled to 50° C. and the catalyst is neutralized with 5.61 g of 50% Hypophosphorous Acid.

EXAMPLE #7

Preparation of PPG-6 N-Methyldiethanolamine Di-Polyricinoleate

To a clean dry stirred tank pressure vessel with Nitrogen inlet and fitted with a distillation column is charged 369.22 g (0.78 moles) of the Propoxylate from example 6, 2130.78 g (1.50 moles) of Polyricinoleic Acid (polymerized Ricinoleic Acid of at least five repeating units) and a catalytic amount (6.25 g) of 50% Hypophosphorous Acid. The batch is heated to 220° C. under Nitrogen sparge and held for one hour after which 100 mm Hg of vacuum is applied. During vacuum, the batch is monitored by measuring the Acid Value. The reaction is considered complete when the Acid Value is preferably less than 5 mg KOH.

EXAMPLE #8

Preparation of PPG-6 N-Methyldiethanolamine Di-Lanolate

To a clean dry stirred tank pressure vessel with Nitrogen inlet and fitted with a distillation column is charged 288.71 g (0.62 moles) of the Propoxylate from example 6, 411.29 g (1.17 moles) of Lanolic Acid (from Croda, Inc.) and a catalytic amount (1.75 g) of 50% Hypophosphorous Acid. The batch is heated to 220° C. under Nitrogen sparge and held for one hour after which 100 mm Hg of vacuum is applied. During vacuum, the batch is monitored by measuring the Acid Value. The reaction is considered complete when the Acid Value is preferably less than 5 mg KOH.

EXAMPLE #9

Methosulfate QUAT of PPG-4 PEG-6 N-Methyldiethanolamine Di-Polyricinoleate

To a clean, dry four neck round bottom flask fitted with Nitrogen inlet, mechanical stirrer, reflux condenser, temperature probe and drop funnel is charged 408.45 g (0.12 moles) of the diester from example 7 and 279.02 g of Dipropylene Glycol as a diluent. The batch is heated to 50° C. and 12.53 g (0.10 moles) of Dimethyl Sulfate is added drop-wise to maintain a temperature below 55° C. After all Dimethyl Sulfate is added the batch is left to react for an additional hour after which the Base Value is checked. The reaction is considered complete when the Base Value is preferably less than 6 mg KOH.

Quaternization of example 8 can also be accomplished as described in this example.

EXAMPLE #10

Preparation of PPG-2 PEG-10 N-Methyldiethanolamine

To a clean, dry stirred tank pressure vessel with Nitrogen inlet is charged 476.06 g (4.00 moles) of N-Methyldiethanolamine, a catalytic amount (5.99 g) of 45% KOH and 1.08 g of NaBH$_4$ as a color preservative. The vessel is then purged with Nitrogen and heated to 110° C. Vacuum is applied for one hour to remove trace amounts of water, after which the temperature is raised to 160° C. Propylene Oxide in the amount of 464.08 g (8.00 moles) and Ethylene Oxide in the amount of 1759.86 (40.00 moles) is added at such a rate so the pressure remains below 50 psig. After all Propylene Oxide and Ethylene Oxide are added, the batch is left to react to constant pressure for an additional 2 hours. After two hours the temperature is lowered to 110° C. and full vacuum is applied for one hour. The reaction mixture is cooled to 50° C. and the catalyst is neutralized with 6.05 g of 50% Hypophosphorous Acid.

EXAMPLE #11

Preparation of PPG-2 PEG-10 N-Methyldiethanolamine Behenate 18-Methyl Eicosanoate To a clean dry stirred tank pressure vessel with Nitrogen inlet and fitted with a distillation column is charged 1392.32 g (2.06 moles) of the Alkoxylate from example 10, 641.10 g (1.96 moles) of 18-MEA Acid (from Croda, Inc.), 666.58 g (1.96 moles) of Behenic Acid and a catalytic amount (6.75 g) of 50% Hypophosphorous Acid. The batch is heated to 220° C. under Nitrogen sparge and held for one hour after which 100 mm Hg of vacuum is applied. During vacuum, the batch is monitored by measuring the Acid Value. The reaction is considered complete when the Acid Value is preferably less than 5 mg KOH.

EXAMPLE #12

Preparation of PPG-2 PEG-10 N-Methyldiethanolamine Di-2-Decyl Tetradecanoate

To a clean dry stirred tank pressure vessel with Nitrogen inlet and fitted with a distillation column is charged 293.00 g (0.43 moles) of the Alkoxylate from example 10, 257.00 g (0.82 moles) of 2-Decyl Tetradecanoic Acid (Jaric I-24 from Jarchem Industries) and a catalytic amount (1.38 g) of 50% Hypophosphorous Acid. The batch is heated to 220° C. under Nitrogen sparge and held for one hour after which 100 mm Hg of vacuum is applied. During vacuum, the batch is monitored by measuring the Acid Value. The reaction is considered complete when the Acid Value is preferably less than 5 mg KOH.

EXAMPLE #13

Methosulfate QUAT of PPG-2 PEG-10 N-Methyldiethanolamine Behenate 18-Methyl Eicosanoate To a clean, dry four neck round bottom flask fitted with Nitrogen inlet, mechanical stirrer, reflux condenser, temperature probe and drop funnel is charged 389.21 g (0.30 moles) of the diester from example 11 and 220.76 g of Dipropylene Glycol as a diluent. The batch is heated to 50° C. and 30.03 g (0.24 moles) of Dimethyl Sulfate is added drop-wise to maintain a temperature below 55° C. After all Dimethyl Sulfate is added the batch is left to react for an additional hour after which the Base Value is checked. The reaction is considered complete when the Base Value is preferably less than 6 mg KOH.

Quaternization of examples 11 and 12 can also be accomplished as described above.

Moisturizing Sunscreen Lotion.

| Ingredients | % W/W |
|---|---|
| Phase A | |
| Quat from Example 9 | 2.0 |
| Behentrimonuim Chloride | 1.0 |
| Cetearyl Alcohol | 4.0 |
| Crodamol OS (Octyl Stearate) | 14.0 |
| Benzophenone 3 | 5.0 |
| Octyl Methoxycinnamate | 7.5 |
| Dimethicone | 1.0 |
| Phase B | |
| Cropeptide W (Hydrolyzed Wheat Protein (and) Hydrolyzed Wheat Starch) | 1.0 |
| Water | 63.5 |

-continued

| Ingredients | % W/W |
|---|---|
| Phase C | |
| Germaben II (preservative) | 1.0 |

Procedure: Combine Phase A and heat to 75° C. In a separate vessel, combine Phase B and heat to 75° C. Add Phase A to Phase B while stirring and continue stirring while allowing to cool to 40° C. Add Phase C and continue cooling to 25° C.

Moisturizing Lotion.

| Ingredients | % W/W |
|---|---|
| Phase A | |
| Quat from example 9 | 3.0 |
| Cetearyl Alcohol | 4.0 |
| Crodamol OS (Octyl Stearate) | 5.0 |
| Cromollient DP3A (Di-PPG-3 Myristyl Adipate) | 5.0 |
| Petrolatum | 3.5 |
| Dimethicone | 3.0 |
| Crodamol SS (Cetyl Esters) | 5.0 |
| Phase B | |
| Water | 69.65 |
| Carbopol 941 (Carbomer) (thickener) | 0.15 |
| Polyester Polyamine from example 2 (neutralizing agent) | 0.70 |
| Phase C | |
| Germaben II (preservative) | 1.00 |

Procedure: Dust the Carbopol 941 from Phase B into the water with mixing. Heat to 75–80° C. and add the polyester polyamine. Combine ingredients from Phase A and heat with mixing to 75–80° C. Add Phase B to Phase A while mixing and allow to cool to 40° C. Add Phase C with mixing and allow to cool to desired fill temperature.

Hair Conditioner.

| Ingredients | % W/W |
|---|---|
| Phase A | |
| Quat from example 13 | 2.5 |
| Cromollient DP3A (Di-PPG-3 Myrystyl Adipate) | 2.0 |
| Incroquat CTC-30 (Cetrimonium Chloride) | 2.0 |
| Phase B | |
| Water | 92.5 |
| Phase C | |
| Germaben II (preservative) | 1.0 |

Procedure: Combine Phase A and heat to 75° C. In a separate vessel, combine Phase B and heat to 75° C. Add Phase A to Phase B while stirring and continue stirring while allowing to cool to 40° C. Add Phase C and continue cooling to 25° C.

Conditioning Shampoo.

| Ingredients | % W/W |
|---|---|
| Phase A | |
| Cromollient SCE (Di-PPG-2 Myreth-10 Adipate) | 4.0 |
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Germaben II (Preservative) | 1.0 |
| Water | 52.0 |
| Phase B | |
| Quat from example 13 | 2.0 |

Procedure: Combine Phase A and heat to 60° C. Add Phase B and continue stirring while allowing to cool to 25° C.

Conditioning Shampoo With UV Protection.

| Ingredients | % W/W |
|---|---|
| Phase A | |
| Cromollient SCE (Di-PPG-2 Myreth-10 Adipate) | 4.0 |
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Germaben II (Preservative) | 1.0 |
| Water | 50.0 |
| Phase B | |
| Quat from example 13 | 2.0 |
| Crodasorb UV-HPP (Polyquaternium 59) | 2.0 |

Procedure: Combine Phase A and heat to 60° C. Add Phase B and continue stirring while allowing to cool to 25° C.

Clear Deodorant Stick.

| Ingredients | % W/W |
|---|---|
| Part A | |
| Sodium Stearate C-1 | 7.7 |
| Incromide CA (Cocamide DEA) | 7.0 |
| Quat from example 5 | 1.5 |
| Propylene Glycol | 58.0 |
| Triclosan | 0.3 |
| Probutyl DB-10 (PPG-10 Butane Diol) | 8.5 |
| Part B | |
| Deionized Water | 17.0 |

Procedure: Combine all Part A ingredients and increase temperature to 70–80° C. using high agitation. Continue stirring for 5–10 minutes once temperature is reached, then slowly start adding Part B over a 5–10 minute period. Pour into molds.

Clear Body Wash.

| Ingredients | % W/W |
|---|---|
| Part A | |
| Deionized Water | 55.9 |
| Sodium Lauryl Ether Sulfate | 20.0 |
| Crosultaine C-50 (Cocoamidopropyl Hydroxysultaine) | 12.0 |
| Disodium EDTA | 0.1 |
| Quat from Example 5 | 2.0 |
| Part B | |
| Incromide CA (Cocamide DEA) | 3.0 |
| Glycerox 767 (PEG-6 Capric/Caprylic Triglycerides) | 3.0 |
| Crothix Liquid (PEG-150 Pentaerythrityl Tetrastearate (and) PEG-6 Caprylic/Capric Glycerides) | 3.0 |
| Part C | |
| Germaben II (Preservative) | 1.0 |

Procedure: Combine Part A with mixing. Combine Part B with mixing and heat to 50° C. Slowly add Part B to A and continue stirring while allowing to cool.

What is claimed is:

1. A personal care product comprising a mixture having a pH of between about 4.0 and about 10.0 and a viscosity of between about 100 to about 300,000 cps, said mixture including at least one personal care ingredient and a diester quat having the Formula I

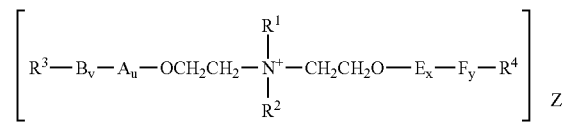

Formula I wherein $R^1$ and $R^2$ are the same or different, branched or straight chain, substituted or unsubstituted, saturated or unsaturated alkyl, cyclic or aromatic groups including between about 1 and about 22 carbon atoms;

A and E are the same or different and may be ethoxy or propoxy and wherein at least one of A or E is propoxy;

u and x may be the same or different and are at least 2 and at most about 80 with the proviso that the majority of alkoxy units in Formula I are ethoxy groups;

B and F may be the same or different and are either of Formula II or Formula III

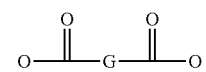

Formula II

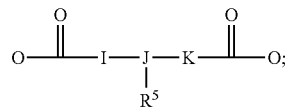

Formula III wherein G is $C_0$ through $C_{36}$ groups which may be substituted or unsubstituted, saturated or unsaturated, straight or branched, alkyl, cyclic or aromatic, I and K are $C_0$–$C_{18}$ groups and J is CH, $R^5$ is H or [—L—COO—$R^6$] where L can be saturated or unsaturated, substituted or unsubstituted, straight or branched, alkyl, cyclic or aromatic and can be a $C_0$–$C_{36}$ group; and v and y may be the same or different and are 0 or 1, wherein at least one v and y is at least 1;

when v equals 0, $R^3$ may be Formula IV and when y equals 0, $R^4$ may be Formula IV

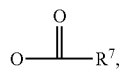

Formula IV a UV protecting group having a carboxy functional group or a poly fatty acid, $R^7$ is the same or different, branched or straight chain, substituted or unsubstituted, saturated or unsaturated alkyl, cyclic or aromatic groups including between about 1 and about 36 carbon atoms;

when v equals 1, $R^3$ may be Formula V or VI and when y equals 1, $R^4$ may be Formula V or VI

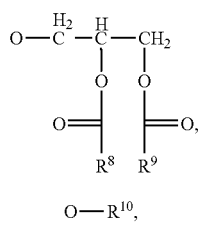

Formula V

Formula VI a UV protecting group ending in a reactive hydroxy group or a poly fatty acid, $R^8$, $R^9$ and $R^{10}$ are the same or different, branched or straight chain, substituted or unsubstituted, saturated or unsaturated alkyl, cyclic or aromatic groups including between about 1 and about 36 carbon atoms; and when v or y is 1 and B or F are Formula III, $R^6$ may be Formula V or VI

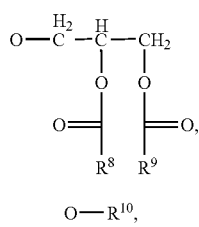

Formula V

Formula VI a UV protecting group ending in a reactive hydroxy group or a poly fatty acid, $R^8$, $R^9$ and $R^{10}$ are the same or different, branched or straight chain, substituted or unsubstituted, saturated or unsaturated alkyl, cyclic or aromatic groups including between about 1 and about 36 carbon atoms; and Z is a counter ion.

2. The personal care product as claimed in claim 1, wherein said mixture has a pH of between about 5.0 and about 9.0.

3. The personal care product as claimed in claim 1, wherein said A or said E is an ethoxy group.

4. The personal care product as claimed in claim 1, wherein $R^1$ is $C_1$ to $C_7$ branched or straight chain, substituted or unsubstituted, saturated or unsaturated alkyl, cyclic or aromatic groups.

5. The personal care product as claimed in claim 1, wherein $R^1$ is $CH_3$.

6. The personal care product as claimed in claim 1, wherein $R^2$ is $C_1$ to $C_7$ branched or straight chain, substituted or unsubstituted, saturated or unsaturated alkyl, cyclic or aromatic groups.

7. The personal care product as claimed in claim 1, wherein $R_2$ is $CH_3$.

8. The personal care product as claimed in claim 1, wherein $R^1$ and $R^2$ are the same group.

9. The personal care product as claimed in claim 1, wherein $R^1$ and $R^2$ are $CH_3$.

10. The personal care product as claimed in claim 1, wherein u is a number from 5 to 30.

11. The personal care product as claimed in claim 1, wherein x is a number from 5 to 30.

12. The personal care product as claimed in claim 1, wherein u and x are the same and are a number from 5 to 20.

13. The personal care product of claim 1, wherein said viscosity ranges from between about 11,000 and about 300,000 cps.

14. The personal care product of claim 1, wherein said personal care ingredient is a surfactant, a quat, a solvent, a UV protecting ingredient, a fragrance, a color, a dye, an emulsifier, a humectant, a polymer or a stabilizer.

15. The personal care product of claim 1, wherein $R^7$, $R^8$, $R^9$ and $R^{10}$ are fatty substituents.

16. A personal care product comprising a mixture having a pH of between about 4.0 and about 10.0 and a viscosity of between about 100 to about 300,000 cps, said mixture including at least one personal care ingredient and a diester quat having the Formula I

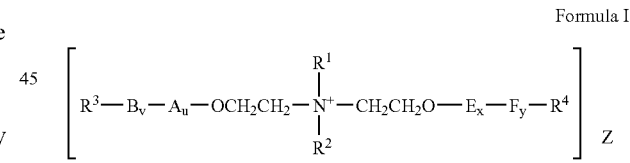

Formula I wherein $R^1$ and $R^2$ are the same or different, branched or straight chain, substituted or unsubstituted, saturated or unsaturated alkyl, cyclic or aromatic groups including between about 1 and about 22 carbon atoms;

A and E are the same or different and may be ethoxy or propoxy and wherein at least one of A or E is propoxy;

u and x may be the same or different and are at least 2 and at most about 80 with the proviso that the majority of alkoxy units in Formula I are propoxy groups;

B and F may be the same or different and are either of Formula II or Formula III

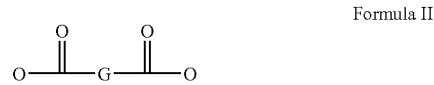

Formula II

-continued

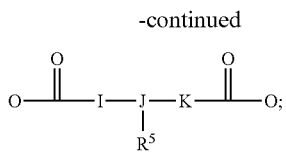

Formula III wherein G is $C_0$ through $C_{36}$ groups which may be substituted or unsubstituted, saturated or unsaturated, straight or branched, alkyl, cyclic or aromatic, I and K are $C_0$-$C_{18}$ groups and J is CH, $R^5$ is H or [—L—COO—$R^6$] where L can be saturated or unsaturated, substituted or unsubstituted, straight or branched, alkyl, cyclic or aromatic and can be a $C_0$-$C_{36}$ group; and v and y may be the same or different and are 0 or 1, wherein at least one of v and y is at least 1;

when v equals 0, $R^3$ may be Formula IV and when y equals 0, $R^4$ may be Formula IV

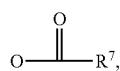

Formula IV a UV protecting group having a carboxy functional group or a poly fatty acid, $R^7$ is the same or different, branched or straight chain, substituted or unsubstituted, saturated or unsaturated alkyl, cyclic or aromatic groups including between about 1 and about 36 carbon atoms;

when v equals 1, $R^3$ may be Formula V or VI and when y equals 1, $R^4$ may be Formula V or VI

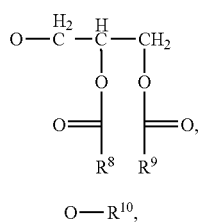

Formula V

Formula VI a UV protecting group ending in a reactive hydroxy group or a poly fatty acid, $R^8$, $R^9$ and $R^{10}$ are the same or different, branched or straight chain, substituted or unsubstituted, saturated or unsaturated alkyl, cyclic or aromatic groups including between about 1 and about 36 carbon atoms; and when v or y is 1 and B or F are Formula III, $R^6$ may be Formula V or VI

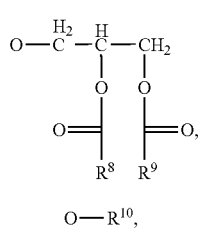

Formula V

Formula VI a UV protecting group ending in a reactive hydroxy group or a poly fatty acid, $R^8$, $R^9$ and $R^{10}$ are the same or different, branched or straight chain, substituted or unsubstituted, saturated or unsaturated alkyl, cyclic or aromatic groups including between about 1 and about 36 carbon atoms; and Z is a counter ion.

17. The personal care product as claimed in claim 16, wherein said mixture has a pH of between about 5.0 and about 9.0.

18. The personal care product as claimed in claim 16, wherein $R^1$ is $C_1$ to $C_7$ branched or straight chain, substituted or unsubstituted, saturated or unsaturated alkyl, cyclic or aromatic groups.

19. The personal care product as claimed in claim 16, wherein $R^1$ is $CH_3$.

20. The personal care product as claimed in claim 16, wherein $R^2$ is $C_1$ to $C_7$ branched or straight chain, substituted or unsubstituted, saturated or unsaturated alkyl, cyclic or aromatic groups.

21. The personal care product as claimed in claim 16, wherein $R_2$ is $CH_3$.

22. The personal care product as claimed in claim 16, wherein $R^1$ and $R^2$ are the same group.

23. The personal care product as claimed in claim 16, wherein $R^1$ and $R^2$ are $CH_3$.

24. The personal care product as claimed in claim 16, wherein u is a number from 5 to 30.

25. The personal care product as claimed in claim 16, wherein x is a number from 5 to 30.

26. The personal care product as claimed in claim 16, wherein u and x are the same and are a number from 5 to 20.

27. The personal care product of claim 16, wherein said viscosity ranges from between about 11,000 and about 300,000 cps.

28. The personal care product of claim 16, wherein said personal care ingredient is a surfactant, a quat, a solvent, a UV protecting ingredient, a fragrance, a color, a dye, an emulsifier, a humectant, a polymer or a stabilizer.

29. The personal care product of claim 16, wherein $R^7$, $R^8$, $R^9$ and $R^{10}$ are fatty substituents.

30. A personal care product comprising a mixture having a pH of between about 5.0 and about 9.0 and a viscosity of between about 100 to about 300,000 cps, said mixture including at least one personal care ingredient and a diester quat having the Formula I

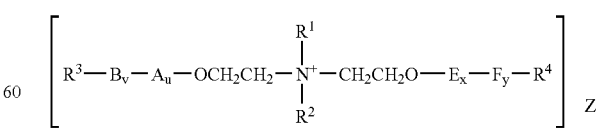

Formula I wherein $R^1$ and $R^2$ are the same or different, branched or straight chain, substituted or unsubstituted, saturated or unsaturated alkyl, cyclic or aromatic groups including between about 1 and about 22 carbon atoms;

A and E are both propoxy;

u and x may be the same or different and are at least 2 and at most about 80, B and F may be the same or different and are either of Formula II or Formula III

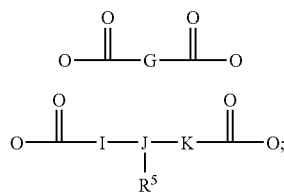

Formula II

Formula III wherein G is $C_0$ through $C_{36}$ groups which may be substituted or unsubstituted, saturated or unsaturated, straight or branched, alkyl, cyclic or aromatic, I and K are $C_0$–$C_{18}$ groups and J is CH, $R^5$ is H or [—L—COO—$R^6$] where L can be saturated or unsaturated, substituted or unsubstituted, straight or branched, alkyl, cyclic or aromatic and can be a $C_0$–$C_{36}$ group; and v and y may be the same or different and are 0 or 1;

when v equals 0, $R^3$ may be Formula IV and when y equals 0, $R^4$ may be Formula IV

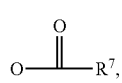

Formula IV a UV protecting group having a carboxy functional group or a poly fatty acid, $R^7$ is the same or different, branched or straight chain, substituted or unsubstituted, saturated or unsaturated alkyl, cyclic or aromatic groups including between about 1 and about 36 carbon atoms;

when v equals 1, $R^3$ may be Formula V or VI and when y equals 1, $R^4$ may be Formula V or VI

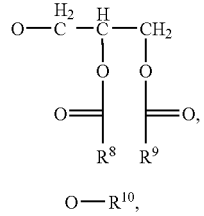

Formula V

Formula VI a UV protecting group ending in a reactive hydroxy group or a poly fatty acid, $R^8$, $R^9$ and $R^{10}$ are the same or different, branched or straight chain, substituted or unsubstituted, saturated or unsaturated alkyl, cyclic or aromatic groups including between about 1 and about 36 carbon atoms; and when v or y is 1 and B or F are Formula III, $R^6$ may be Formula V or VI

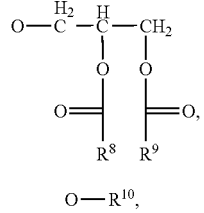

Formula V

Formula VI a UV protecting group ending in a reactive hydroxy group or a poly fatty acid, $R^8$, $R^9$ and $R^{10}$ are the same or different, branched or straight chain, substituted or unsubstituted, saturated or unsaturated alkyl, cyclic or aromatic groups including between about 1 and about 36 carbon atoms; and Z is a counter ion.

* * * * *